United States Patent [19]

Moriya et al.

[11] Patent Number: 5,028,906
[45] Date of Patent: Jul. 2, 1991

[54] HUMIDITY SENSOR

[75] Inventors: Yoshio Moriya, Atsugi; Ryuji Kojima, Tokyo; Kentaro Nagano, Yokohama; Kazuhiro Ishikura, Hiratsuka; Yasuo Imai, Yokohama; Yasunobu Matsushima, Kawasaki, all of Japan

[73] Assignee: Nihon Parkerizing Co., Ltd., Tokyo, Japan

[21] Appl. No.: 256,007

[22] Filed: Oct. 11, 1988

[30] Foreign Application Priority Data

Oct. 12, 1987 [JP] Japan .............................. 62-254596
Oct. 19, 1987 [JP] Japan .............................. 62-261857

[51] Int. Cl.$^5$ ............................................ G01W 1/00
[52] U.S. Cl. ................................. 338/35; 73/336.5
[58] Field of Search ................. 73/336.5; 338/35

[56] References Cited

U.S. PATENT DOCUMENTS 3,523,244  8/1970  Goodman .......................... 73/336.5
4,052,691 10/1977  Nagano ................................ 338/35
4,343,688  8/1982  Harwood .............................. 338/35
4,419,889 12/1983  Misto ................................ 73/336.5
4,497,701  2/1985  Murata ............................... 73/336.5
4,562,725  1/1986  Oka .................................. 73/336.5

Primary Examiner—Sam Silverberg
Attorney, Agent, or Firm—Armstrong, Nikaido, Marmelstein, Kubovcik, & Murray

[57] ABSTRACT

This invention concerns a humidity sensor wherein a chemical conversion coating, giving attention to the property that it undergoes an impedance decrease with adsorption of moisture, is used as humidity sensing element which is characterizied by an extremely short electrode distance, greatly improved sensitivity, high speed response, stable performance over a long period of time, high reliability and cheaper production cost.

The principal point that characterizes the humidity sensor in this invention is that the chemical conversion coating deposited on the metal surface with or without an electrolysis application, is made usable as a humidity sensing element. For the chemical conversion coating, such coatings as phosphate, oxalate, titanium fluorocomplex, chromium phosphate and non-chromium types are used.

On top of this chemical conversion coating, application of a humidity sensing film is effected to further improve humidity sensing performance.

28 Claims, 22 Drawing Sheets (1) OXALATE FILM
(2) TITANIUM FLUORIDE COMPLEX SALT FILM
(3) OXALATE FILM + $NaPO_3$ Fig. 16
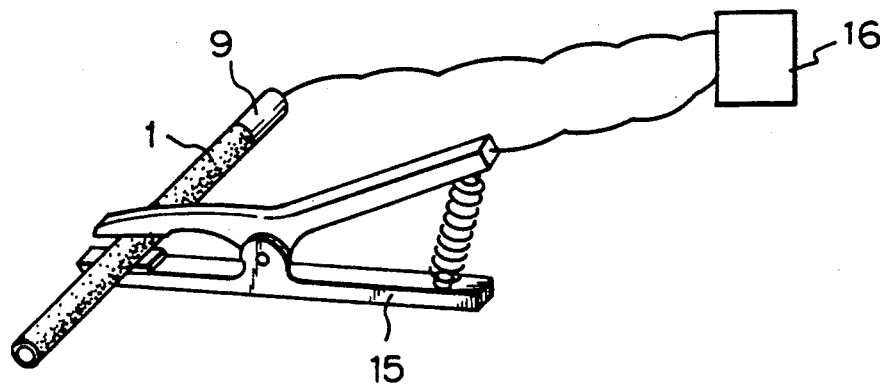
Fig. 17
Fig. 15A   Fig. 15B
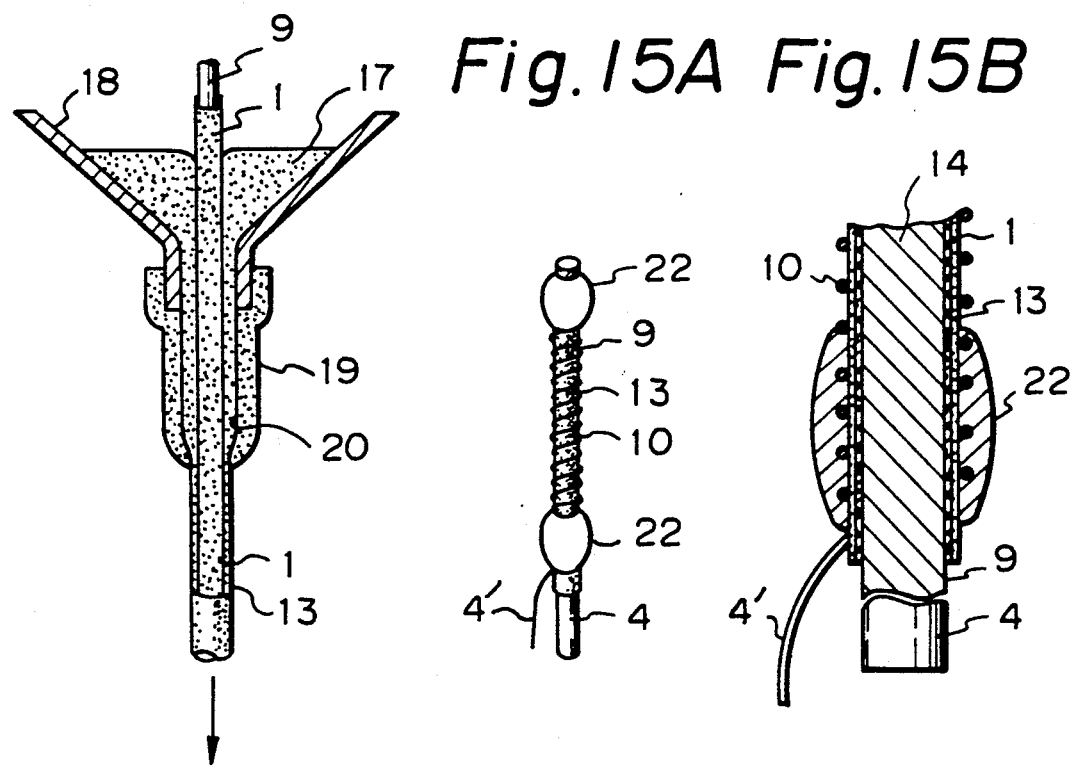

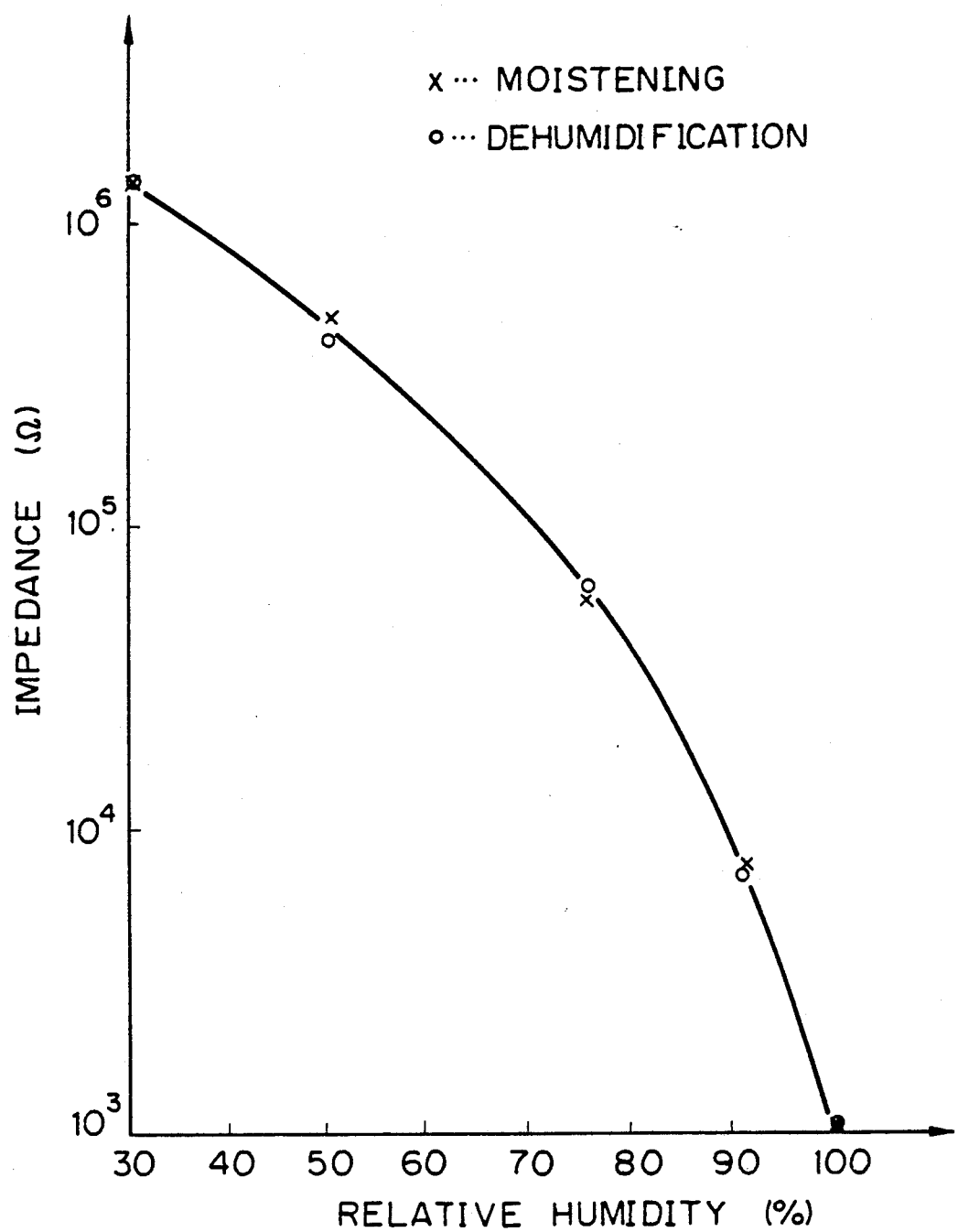

HUMIDITY SENSOR

BACKGROUND OF THE INVENTION

1. Industrial fields

This invention concerns a humidity sensor. The humidity sensor in this invention includes, besides an ordinary humidity sensor, a wide range of sensors applicable to various purposes such as dew condensation sensor, rain drop sensor etc.

2. Prior art

Among humidity sensors hitherto used, there are, for example, hair hygrometers and wet and dry bulb hygrometers which are in wide use for controlling/preventing dew condensation on anti-cloud glass used for autovehicles and aircrafts.

However, those hitherto in use need manual maintenance and moreover lack reliability. Therefore, their practical application is not satisfactory.

In view of this, recently, as can be seen in Japanese Patent Publication Sho 55-49705, humidity sensors using high molecular substances or ceramics as humidity sensing elements have been developed, some of which are already in practical use.

Conventional humidity sensors for which a high molecular substance is used as a humidity sensing element afford good sensitivity but have the following drawbacks: they are easily contaminated and their life is short. The one using ceramics is of good stability and capable of vaporizing contaminant particles by heating. In contrast to these advantages, the disadvantages are high level of labor and manufacturing cost, poor adhesion between the element and base plate, poor sensitivity, complicated circuit configuration, short life of the sensor, slow response speed etc. Indeed, these drawbacks have up to now prevented a hygrometer or humidity sensor from propagating into use fields in general terms.

A complementary explanation on this point using FIG. 1A and FIG. 1B is as follows. The humidity sensing element 7, made of semiconductive ceramics, is manufactured by a high pressure press forming of a raw oxide powder mixture, which then is baked at a high temperature to a sintered compact.

This process requires the following stages; compounding of raw materials, press forming, and high temperature sintering. Meanwhile, the humidity sensing element to be coated on the base plate requires raw material compounding, flame spraying or printing, and baking. These stages not only require experience and high skill but costly production facilities have to be used such as a press machine, baking oven, flame spraying machine, printer and so on.

It is notable here that, as the electrically insulated base plate over which the humidity sensing element is to be coated, an alumina base plate or heat-resistant glass base plate is used.

As explained above, manufacturing a humidity sensing element is done by using a mixture of raw oxide powder and ceramics or heat-resistant glass base plate, which then requires complicated processing stages and costly manufacturing. The final manufacturing cost becomes very high.

This is the reason why the use of humidity sensors has not been more widespread.

The humidity sensing element 1, manufactured this way is of high electric resistance or impedance, a parameter corresponding to humidity. Therefore, in order to determine the resistance by making a connection with an outside electronic circuit, a device is made to reduce inter-electrode resistance by giving opposing electrodes 2 and 2' a comb-like structure, owing to which their opposing portions are given more length. These comb-like electrodes are connected with the terminal electrodes 3 and 3': 3 and 3' are connected respectively with lead wires 4 and 4' to be connected with the outside electronic circuit, wherein the connection is done by soldering at electrode terminal posts 5 and 5' or by electric welding 8 and 8'.

The comb-like structured opposing electrodes 2 and 2' are prepared by print-application of gold paste or ruthenium oxide paste on humidity-sensing element 1 or base plate 7, followed by firing. However, due to the current printing technology and paste spreading, it is hard to maintain a prescribed interelectrode distance. Where this distance is less than 0.3 mm, there is the possibility of a short-circuit between opposing electrodes.

Accordingly, when the application of high price paste and a printing technology is nevertheless unable to provide the interelectrode resistance with the required value for the electronic circuit design, it is necessary to make the resistance smaller by increasing the number of electrodes or by making the electrode length greater, whereby the sensor has been restricted by designing/minimizing the shape.

Further, in order to have a linkage between the sensor and the electronic circuit by connecting lead frames or lead wires 4 and 4' with electrode terminals 3 and 3', electrode terminal pastes 5 and 5', previously printed/baked with silver or gold paste, are provided. When such portions are soldered, the flux used there often spatters and penetrates into the humidity sensing element, giving rise to a bad effect on the performance thereof. To avoid such contaminations, designing certain countermeasures in advance to protect the humidity sensing element 1 from contamination or taking necessary measures to remove contaminants after soldering, should be done. Any way, burdensome steps are required, which is a cause of lowered productivity and quality.

In the case of soldering at 8 and 8' for the connection, the problem of flux does not exist. However, due to the difficulty of inspecting whether or not the connection is done perfectly, poor circuit continuity might cause trouble after making.

Consequently, in any case, the stage of connecting the sensor electrode terminal 3 and 3' with lead frame or lead wire 4 and 4' is of prime importance as it might affect the performance of the sensor by reducing productivity and yield.

As explained above re the humidity sensor hitherto in use, the humidity sensing element thereof requires high manufacturing cost. Further, in view of the high electric resistance of this element, the device is made so as to alleviate this difficulty by giving opposing electrodes a comb-like structure. This structure also needs costly materials and high technology. Consequently, the manufacturing cost is raised and minimizing the sensor size is hindered. Moreover, the necessary treatment of electrode terminals for connecting the sensor and the outside electronic circuit often cause the sensing performance to deteriorate, and productivity and yield are lowered, thereby again causing the manufacturing cost to rise.

The purpose of this invention is to provide a solution to the problems described above, which exist in the technology hitherto in use in relation to humidity sensors, including the manufacturing method for the sensor and sensing element.

SUMMARY OF THE INVENTION

This invention has been made to provide the solution to the above mentioned problems, wherein a chemical conversion coating, having the property that its impedance lowers with adsorption of moisture, is used as a humidity sensing element.

First, the fundamental conception for this invention is described hereinunder. The inventors of this invention preliminarily carried out a study on phosphate compounds, long since known as rust preventives or as lubricants, while paying attention to their physical properties.

Phosphate coatings, as indicated in Examples 1 to 5, are formed on a substrate metal surface by making a suitable metal such as steel or galvanized steel, come in contact by dip or spray, with a treatment solution containing phosphoric acid as a principal constituent and one or more kinds of ions of zinc, manganese, calcium, aluminum, nickel etc. Such phosphate coatings have hitherto been used merely for rust prevention or as a paint base coating, or in the case of cold forming as a lubricant film.

However, as a result of a study carried out by the inventors on the characteristics of phosphate coating, it has been revealed that said coating also has excellent performance as a humidity sensor.

As for phosphate coatings, there are various types, such as zinc phosphate, calcium phosphate, zinc/manganese phosphate, zinc/calcium phosphate, iron phosphate, and aluminum phosphate. Every one of them is acknowledged to be capable of functioning as an excellent humidity sensor.

The thickness of the phosphate coating is of a 0.1 to 120 $\mu$ level. Since this coating is formed on a metal surface, this invention constitutes a humidity sensor consisting of one of the electrodes being a substrate metal.

The inventors have also made a study on the physical properties of other chemical conversion coatings such as oxalate coating and fluoro-complex salt coating, which are known as conversion coatings for titanium or stainless steel and as lubrication coatings for titanium.

Oxalate coating, as indicated in Example 6 for instance, is a coating formed on stainless steel wherein stainless steel is dipped in a treatment solution containing oxalic acid as a main constituent, as well as nitric acid and hydrofluoric acid.

Titanium fluoro-complex salt coating, as indicated in Example 7 for instance, is a coating formed on a titanium metalsurface wherein titanium is dipped in a treatment solution containing sodium hydrogen fluoride ($NaHF_2$) as a main constituent (sometimes, it contains metallic ions such as zinc and manganese in small quantities). This coating has hitherto been used as a lubricant film for cold rolling of titanium metal.

Furthermore, the inventors also found out that other chemical conversion coatings such as those in use as paint base coatings on, or rust prevention of, aluminum or its alloys also have humidity sensing properties. To mention some in general, they are phosphate coating, chromate coating, non-chromate coating, roll-on type chromate coating etc. Out of these, such coatings as phosphate, titanium-tannic acid complex salt, zirconium-phytic acid complex salt and roll-on type chromate, have been found to have good humidity sensing properties. By using these coatings, the humidity sensor has been prepared.

Further, these coatings have been used as carriers of the humidity sensing agent to prepare the humidity sensing element. Chromium phosphate coating, as indicated in Example 9 for instance, is a coating formed on aluminum or its alloys wherein a substrate metal is treated with dipping in, or the spraying on of, a treatment solution containing chromic acid and phosphoric acid as the main constituents, and hydrofluoric acid or its double salts. This chromium phosphate coating has been used for rust prevention or as a paint base coating on aluminum.

Titanium-tannic acid complex salt coating, as indicated in Example 10 for instance, is a coating formed on aluminum or its alloys wherein a substrate metal is treated with dipping in, or the spraying on of, a treatment solution containing titanium and tannic acid as the main constituents, and hydrofluoric acid or its double salts.

This coating has been used as a paint base coating for aluminum or its alloys (Japanese patent Publication Sho 53-156867).

Zirconium phytic acid complex salt coating, as indicated in Example 11 for instance, is a coating formed on aluminum or its alloys wherein a substrate metal is treated with dipping in, or spraying of, a treatment solution containing zirconium and phytic acid as the main constituents and hydrofluoric acid or its double salts. This coating has hitherto been used as a paint base coating on aluminum or its alloys (Japanese Patent Publication Sho 55-19315).

The roll-on type chromate coating, as indicated in Example 12, is a coating formed on aluminum or its alloys, wherein a substrate metal is treated with roll coating of a treatment solution comprising the constituents in the above mentioned chromium chromate treatment solution and containing either one of colloidal silica or waterborn acrylic resin or both. This coating has hitherto been used for rust prevention of, or as a paint base coating on metals (Japanese Laid-open Patent Sho 60-218483, Japanese patent Application Sho 61-163559).

Chromate coating or non-chromate coating as such has a thickness level of 0.2 $\mu$ to a few $\mu$. Since the coating is formed on aluminum or its alloy surface, the constitution of the humidity sensor in this invention is made by fastening two sets of thus conversion-coated wires around each other, of which one is used as a metal electrode, and the other as an opposite electrode.

Chemical conversion coating is widely used as a base coat for painting because it improves adhesion with the paint and at the same time provides the substrate metal with enhanced corrosion resistance. By means of putting a coating of humidity film over a chemical conversion coating, which itself has a humidity sensitive function, the inventors have made it possible for the humidity sensor element to withstand a loss of circuit continuity due to coated film destruction as well as to have improved corrosion resistance and enhance the humidity sensing performance. Further, in order to offer an improved humidity sensor with low production cost and minimized size, the structure of the humidity sensor, consisting of a humidity element manufactured on the basis of the above mentioned chemical conversion coating, has also been elaborated, so that the required electrode terminal processing does not cause a degradation in sensor performance nor a decrease in productivity or product yield. For this purpose, a structure consisting of a metal electrode coated with a humidity sensing film as the 1st electrode, and the opposite electrode which is made to come in contact with said film, as the 2nd electrode, has been created.

EFFECTS OF THE INVENTION

As described above, the humidity sensor offered by this invention is constituted with a chemical conversion coating that functions as the humidity sensing element and consequently can afford excellent effects as described hereunder.

1. Owing to an extremely thin coating, as small as 0.5 to 10μ, the electrode distance can be made far smaller than that in conventional ones. This is a crucial factor for the sensor to perform with predominantly improved sensitivity and quick response.

2. The characteristics are stably preserved over a long period of time, so that the sensor can be provided with long life and greatly improved reliability.

3. Expensive apparatuses and costly manufacturing process, such as plasma sprayers and baking ovens, can be dispensed with, so that the manufacturing cost can be reverted to a minimum.

4. In the case of making use of oxalate coating or titanium fluorocomplex salt coating as a humidity sensing element, a substrate of stainless steel or titanium can be used, with superior rust resistance and durability.

5. In the case where chromate coating or non-chromate coating is used as a humidity sensing element, aluminum or its alloys used as a base metal element can enjoy excellent corrosion resistance and durability.

6. Referring to the description in the case of humidity detection as an example, the humidity sensor in this invention is, besides those above mentioned, usable as dew sensor, rain droplet sensor etc. for which the usages are, for example, prevention of loss of smooth running of video tape decks due to dewing, control of clouding prevention in heating automobile rear window glass, hydrostat for pipings, and many other humidity detectors. Furthermore, since this sensor is available in a tiny size and at a low price, the usage can cover various and wide ranges even for such throwaway articles as paper diapers for babies and the older people confined to bed.

In the case of those electrodes having a humidity sensitive coating formed over a conversion coating made of the humidity sensors offered by this invention, they are given a combination of the following effects.

1) Humidity sensitive film, formed over a phosphate coating by applying a paste prepared with phosphate and thermosettable waterborne resin, tightly adheres onto the humidity sensing element by means of anchoring its roots into the fine pores that the underlying phosphate coating has abundantly and widely. The coating thus formed also functions to rectify circuit continuity failures of phosphate coating.

It also prevents coating destruction taking place when the opposite electrode is contacted, leading to improved product yield.

Also, through providing the coated film with hygroscopic properties, it is possible to convert the above-mentioned dew sensor to a humidity sensor capable of responding to lower humidity. Further, by filling up its interstices and thereby fixing the opposite electrode coil, the element can be protected from electrode dislodgement due to impact and thermal change with no loss in long-term performance.

2) In the case of using a humidity-sensible film coating formed by dipping in an emulsion liquid containing colloidal silica/acryl composite particles, its high water vapor permeability makes it possible to prevent coating failures, and thereby contributes to the inexpensive manufacturing of humidity sensor elements, which results in a wide range of application, even to such throwaway type articles as paper diapers as noted earlier.

In regard to using phosphate coating formed on a copper base substrate material as a humidity sensible element, it has a combination of the following effects and advantages. The superiority thereof in the adhesion, sensitiveness and response speed together with low price and stability owing to the use of copper, has made it possible to manufacture a humidity sensor at a low cost.

In the case where the electrode structure is modified, the following effects, which are superior to the prior art, are created.

1) It does not need a comb-like structured electrode, therefore, the contact between the opposite electrode and the humidity sensing element can be made on both whole faces.

2) The electrode terminal lead wire and the electrode can be formed as an unified body, therefore, there is no need of terminal preparation work by adhesion-connecting lead frame or lead wire with the electrode terminal. This process is laborious as it requires soldering or welding.

The effect of eliminating this process is great from the aspects of productivity and quality improvement.

3) As set forth in Example 5, the a sensor can be made by twisting the metal electrode and the opposite electrode around each other using the twisted area as the humidity sensing part and the electrode wire itself as the terminal lead wire. In consequence, the manufacturing is extremely easy and inexpensive. A structure such as this with a smaller wire diameter, can reduce the whole shape to an extreme minimum, offering a variety of usages.

From the description abovementioned, it is evident that coating on substrate metal with crystal powder, having the same composition as in the case of a chemical conversion coating on a metal surface, or even with sludge generated in a chemical conversion treatment bath, may provide the same effect.

DESCRIPTION OF THE DRAWINGS

FIG. 15 indicates the electrode of the humidity sensor to be applied to the sample in Example 14. FIG. 15A is a schematic view showing the appearance of the humidity sensor. FIG. 15B is a part of the sensor magnified at a vertical section.

FIG. 16 is a schematic view of the resistance determination terminal.

FIG. 17 is a front view magnified at a horizontally cut section.

FIG. 19 indicates the electrode for the humidity sensor to be applied to the sample in Example 15. FIG. 20 and FIG. 21 are the humidity sensing characteristic figures obtained by measuring the sensing characteristic figures of the sample in Example 15.

FIG. 22 indicates the electrode of the humidity sensor to be applied to the samples in Example 16.

FIG. 24 indicates the electrode of the humidity sensor to be applied to the samples in Example 17.

As noted above, FIGS. 2, 5, 6, 8, 15, 19, 22, 24 and 27 are parts of the structure of the humidity sensor in this invention. The numerals attached to these figures have the following significations in common. 1: humidity sensing element 2: comb-shaped electrode 3: electrode terminal 4: lead wire 5: electrode terminal and portion (for soldering) 6: soldering 7: base plate 8: electric welding 9: metal electrode 10: opposite electrode 11: openings 12: metal fixture 13: cover 14: ventilation window 15: measurement terminal 16: A.C. resistance 17: paste 18: paste holder 19: nozzle 20: nozzle opening 21: electrode wires collected 22: fixer tube 23: fine holes 24: soluble phosphate

FUNCTION

Figure 1A:
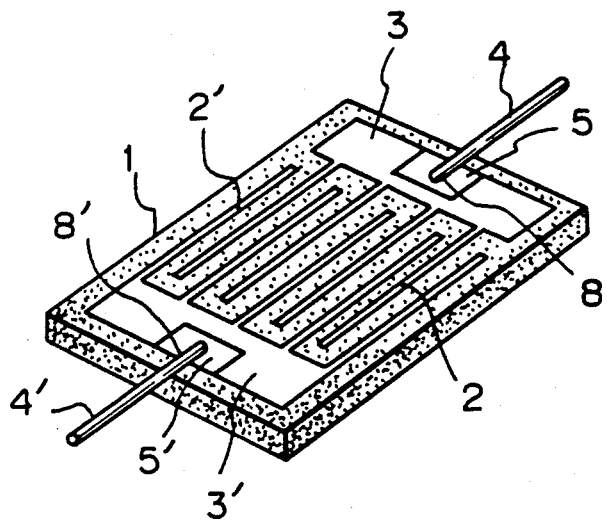
FIG. 1A, FIG. 1B respectively are the schematic views of the humidity sensors in prior art.
Figure 1B:
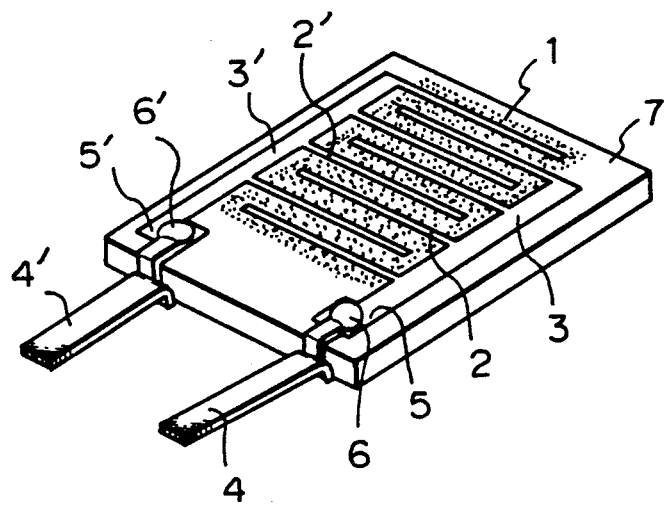

The function of phosphate coating, oxalate coating, and chromium phosphate coating etc. according to this invention and as described in the Examples is discussed hereunder from a chemical point of view.

1) Phosphate coating

The coating components that form a phosphate coating such as $Zn_3(PO_4)_2 \cdot 4H_2O$ (Hopeite), $Zn_2Fe(PO_4)_2 \cdot 4H_2O$ (Phosphophyllite), $Zn_2Ca(PO_4)_2 \cdot 2H_2O$ (Scholzite) etc. are hydrolyzed to a slight extent from moisture, and a description of the chemical reaction thereof proceeds to the right as indicated in the following formulas. As a result, a metal ion is liberated giving ionic conductivity. When the water is gone, a reversible reaction to the left takes place, giving electric insulation. Humidity is measured according to the impedance change.

$$Zn_3(PO_4)_2 \cdot 4H_2O \rightarrow Zn^{2+} + 2HZnPO_4^- + 4H_2O \quad (1)$$

$$Zn_2Fe(PO_4)_2 \cdot 4H_2O \rightarrow Fe^{2+} + 2ZnPO_4^- + 4H_2O \quad (2)$$

$$Zn_2Ca(PO_4)_2 \cdot 2H_2O \rightarrow Ca^{2+} + 2ZnPO_4^- + 2H_2O \quad (3)$$

2) Oxalate coating

Oxalate coating is formed according to the chemical conversion reaction, in which iron dissolved as indicated in equation (4) reacts with an oxalate ion as indicated in equation (5) to form ferrous oxalate coating.

Since oxalate coating is used for treating stainless steel, oxalate reacts with nickel or chromium as shown in equations (6), (7).

$$Fe \rightarrow Fe^{2+} + 2e^- \quad (4)$$

$$Fe^{2+} + C_2O_4^{2-} = FeC_2O \quad (5)$$

$$Ni^{2+} + C_2O_4 = NiC_2O_4 \quad (6)$$

$$2Cr^{3+} + 3C_2O_4^{2-} \rightarrow Cr_2(C_2O_4)_3 \quad (7)$$

Nickel oxalate, being insoluble, becomes a constituent of the coating together with ferrous oxalate, but chromium oxalate is soluble and not incorporated in the coating.

Note here that oxalate coating as the main component in a humidity sensor element, primarily consists of $FeC_2O_4$ and $NiC_2O_4$.

These elements undergo a dissociation reaction into ions with moisture as shown in equations (5) and (6) that proceed to the left, liberating metal ions and oxalate ions which give electroconductivity. When the water is gone, the equation proceeds to the right, resulting in electric insulation. Such change is taken in terms of impedance which are converted to humidity.

3) Titanium fluorocomplex salt

The chemical reaction for forming titanium fluorocomplex salt coating occurs according to equation (8) which indicates that dissolution of titanium takes place and this titanium reacts with sodium hydrogen fluoride to form on a titanium surface barely watersoluble sodium titanium fluoride.

$$Ti + 3NaHF_2 = Na_3TiF_6 + 1.5H_2 \quad (8)$$

In this case, the coating as the main component of the humidity sensor element consists primarily of sodium titanium fluoride.

This element undergoes a reversible reaction of dissociation into ions liberating a sodium ion and fluorocomplex ion, which give electroconductivity. When the water is gone, equation (9) proceeds to the left and electric insulation results. This change is measured in terms of impedance which is converted to humidity.

$$Na_3TiF_6 = 3Na^+ + TiF_6^{3-} \quad (9)$$

4) Chromium phosphate coating

Chromium phosphate coating is formed according to the chemical conversion coating as follows.

Chromic acid in the treating bath is reduced to chromium hydroxide as indicated in equations (10) and (11) which reacts with phosphoric acid to form barely soluble chromium phosphate; equation (12). Aluminum phosphate is produced as shown in equation (13) and basic aluminum oxide is produced as shown in equation (14).

Accordingly, the components that constitute chromium phosphate coating are aluminum phosphate and basic aluminum oxide.

$$2Al + 6HF = 2AlF_3 + 6H \quad (10)$$
$$6H + 2CrO_3 = 2Cr(OH)_3 \quad (11)$$
$$Cr(OH)_3 + H_3PO_4 = CrPO_4 + 3H_2O \quad (12)$$
$$Al + H_3PO_4 = AlPO_4 + 3H \quad (13)$$
$$AlF_3 + 2H_2O = AlO(OH) + 3HF \quad (14)$$
$$CrPO_4 = Cr^{3+} + PO_4^{3-} \quad (15)$$
$$AlPO_4 = Al^{3-} + PO_4^{3-} \quad (16)$$

Chromium phosphate coating as the main component of this humidity sensor element consists primarily of $CrPO_4$ and $AlPO_4$ as noted above. As the element constituents undergo a reversible dissociation reaction into ions with water, that is, when equations (15) and (16) proceed to the right, these substances produce metal ions and a phosphate ion which give an electroconductivity and when these reactions proceed to the left, electric insulation is produced. This change is measured in term of impedance which is converted to humidity.

5) Titanium-tannic acid complex salt coating.

Though the formation reaction is not clearly known as yet, titanium-tannic acid complex salt coating is presumed to be comprised of aluminum oxide and titanium-tannic acid complex as the principal components.

This coating ionizes into titanium cation and tannic acid anion with water, though to a very slight extent. After the water is gone, it resumes the original complex form. This reversible dissociation reaction is measured in terms of the impedance change.

6) Zirconium-phytic acid complex salt coating.

Though the formation reaction is not yet clearly known, zirconium-phytic acid complex coating is presumed to be comprised of aluminum oxide and zirconium-phytic acid complex as the principal components. This coating liberates zirconium cation and phytic acid anion with water, though to a very slight extent. When the water is gone, it resumes the original complex form.

This reversible dissociation reaction is reflected in terms of impedance change.

7) Roll-on type chromate coating.

In this case, the primary components are chromium is phosphate, colloidal silica and acrylic resin.

The impedance change takes place due to the behavior of moisture on chromium phosphate, as described earlier, and on colloidal silica and acrylic resin.

In the invention of the humidity sensor with a humidity sensible element formed on a metal substrate, the structure is designed so that almost all the surface area of the humidity sensing element coated on the metal electrode, comes in contact with the opposite electrode. Consequently, it is possible to achieve precise humidity detection.

Also in the case of the humidity sensor structure in this invention where a wire-shaped metal electrode and an opposite electrode are wound around each other, these wound-around portions provide the contact between the two, due to which exact humidity detection can be carried out.

For the humidity sensor element in the abovementioned structure, any well-known element is usable. However, the use of phosphate coating obtained by chemical conversion treatment as a humidity sensor element, makes it possible to manufacture a humidity sensor of extreme sensitivity and high precision owing to the excellent hygroscopicity/hydrophilicity given by the numerous/fine pores involved in phosphate coating.

Moreover, in the case where a watersoluble phosphate of iron oxide is impregnated and retained in said fine pores, it is possible to adjust the resistance of the sensor. Thus, it has been made also possible to convert a dew sensor to a humidity sensor. Note here that the substances retained in the fine pores do not flow out owing to capillarity. This provides a long term life warranty.

In the case of the structure of the humidity sensor in this invention where the metal electrode coated with the humidity sensing element by conversion treatment, is made to contact the opposite electrode at that element, formation of a humidity sensing film layer on that element takes place. This layer not only repairs the defects of the humidity sensing element in terms of circuit continuity, which take place during the conducting chemical conversion treatment, but also reinforces the coating and thus prevents the circuit continuity defects due to the destruction of coating, from taking place is when the opposite electrode is set to contact the metal electrode.

In the case of applying this invention to a humidity sensor with the structure of a cylindrical metal electrode wound around with a wire-shaped opposite electrode, the formation of the humidity sensing film layer follows the following order.

1) After the formation of the film layer, the opposite electrode is wound around.
2) After the opposite electrode is wound around, forming the film layer follows.
3) After 1), further formation of the film layer is effected, 1) to carry out the repair of the humidity sensor element, 2) to fix the opposite electrode and 3) to carry out the repair and fix the opposite electrode. In 1) and 3), the opposite electrode is made to contact the humidity sensing film layer and in 2) the opposite electrode directly contact the humidity sensor element so as to perform precise humidity detection.

In the abovementioned structure, the phosphate coating is used as a humidity sensing element for the reason that, phosphate coating, $Zn_3(PO_4)_2.4H_2O$(Hopeite), receives ionization to a slight extent by moisture as shown in (30).

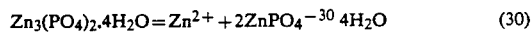

$$Zn_3(PO_4)_2.4H_2O = Zn^{2+} + 2ZnPO_4^{-3} \; 4H_2O \qquad (30)$$

As this equation proceeds to the right, the metal ion is liberated to ionic conductivity. When the water is gone, the reaction reverses to the left, to create electric insulation.

Such property is not only given by a phosphate conversion coating but also by other conversion coatings such as chromate coating and non-chromate coating which are usable as humidity sensible coating in the present invention.

The humidity sensing film layer is the one coated and caked with phosphate powder over the humidity sensing element using resin as a binder.

DESCRIPTION OF THE EXAMPLES

Based on the drawings, a description of the Examples is made hereunder to explain this invention in more detail, in terms of the chemical conversion coating to be used as a humidity sensible element, the structure and manufacture of humidity sensible film, as well as the structure of electrode.

EXAMPLE 1

FIG. 2 indicates the structure of the humidity sensor in this example, of which 2A and 2B are for the manufacturing process. A metallic material was punched out to take the shape in FIG. 2A, measuring 100mm×10mm×0.6mm for instance, on which a phosphate coating was applied to manufacture the metal electrode 9. The opposite electrode 10 was, as indicated in FIG. 2B, manufactured by punching out 0.3mm thickness phosphor bronze to 11mm×7mm, both sides of which are provided with as many openings as 84. By inserting the metal electrode 9 into the interior of the opposite electrode 10, and then applying the metal fixture 12 as indicated in FIG. 2D, the humidity sensor is completely assembled. Note here that 4 or 4' is the electrode terminal whose dimension is of 0.3mm×0.5mm×10mm, in this case.

Figure 2A:
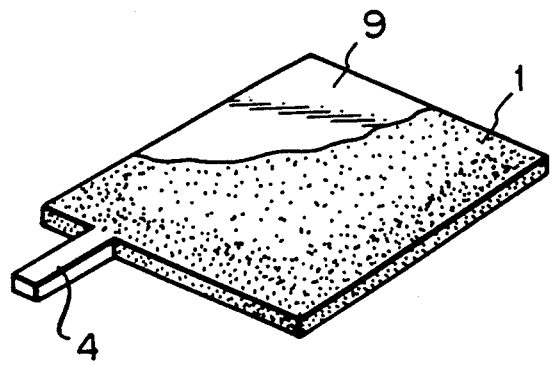
FIG. 2A to FIG. 2D are the schematic views which indicate the structures of the humidity sensors of this invention corresponding respectively to Examples 1 to 4.
Figure 2B:
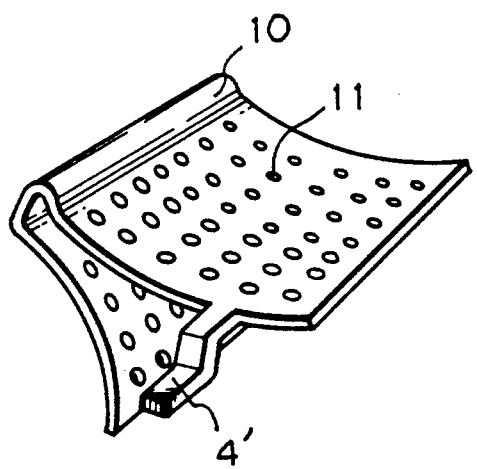
Figure 2C:
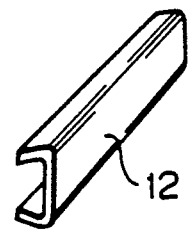
Figure 2D:
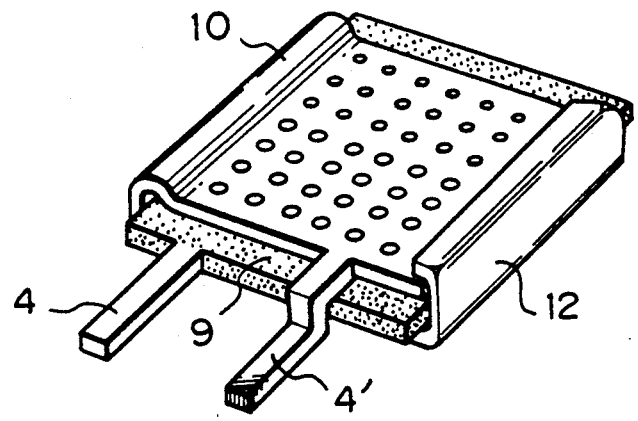

Elastic material was selected for the opposite electrode so it would be flexible in an outward direction, as indicated in FIG. 2B. This facilitated giving a suitable contact force between the humidity sensing element 1 and the opposite electrode 10 when the electrode 9 was insert-fixed into the electrode 10 with metal fixture 12. The openings 11 provided in the opposite electrode 10 are for the purpose of making the moisture reach the humidity sensing element 1 with ease. As an alternative or in addition thereto, it is also useful to zigzag the margin of the opposite electrode so as to give more length of contact.

As an alternative to the case of FIG. 2B, it is also possible to merely overlay the opposite electrode 10 onto the metal electrode 9 and to tightly fix them together.

With the adsorption of moisture, the humidity sensing element 1 with adsorption of moisture varies in the impedance, depending on the amount of moisture. Therefore, by connecting the lead wire with an outside resistance-measuring circuit (not indicated), and from reading the electric resistance to the thickness direction of the humidity sensing element set between the two electrodes, the change of humidity can be determined. The humidity sensing element 1, consisting of a phosphate coating, is an extremely thin film having a thickness of 10 $\mu$ order, so that the resistance thereof is far smaller than in the case where a conventional comb-like shaped electrode is used.

The reason why ferrous material is used for the metal electrode in FIG. 2 is that it is suitable for receiving a conversion treatment to enable phosphate coating to be used as the humidity sensing element. Besides, zinc plating, copper, nickel and stainless steel are usable as the metal electrode, because of the formability thereon of phosphate coating.

On the other side, the reason phosphor bronze is used as the opposite electrode 10 is that the contact resistance between the humidity sensing element and the opposite electrode can be kept at a minimum with reduced fluctuation. Provided that this can be attained, no restriction is given in the invention. In the case where a corrosive environment should be taken into account, nickel plating, gold plating or other precious metal platings are also effective.

Further, in the case where the humidity sensing element on the metal electrode is a thin coating or subjected to partial disconnection which might cause a short-circuit of electrodes, though rarely seen, the opposite electrode with phosphate coating, not only is capable of completely preventing such accidents but also it is the most suitable measure against corrosion.

Further, since phosphate coating can be easily deposited from an aqueous liquid to form on the surface of iron, copper, nickel or zinc plated ferrous material, it may be said that this coating is an inexpensive material to be used for coating the opposite electrode.

Next, the structure and manufacturing process of conversion coating as a humidity sensible element will be explained.

A steel sheet (gauge, 0.3mm), JIS G-3141 SPCC, was used as a substrate which was at first degreased with Fine Cleaner 4360 (product of Nihon Parkerizing Co, Ltd., hereinafter referred to as "Our product'"): 2% aqueous solution, at 70° C. of liquid temperature, 5 min dipping, then water rinsed. Thereafter it is was pickled by dipping in 10% HCl at 25° C. for 1 min and then water rinsed. After that conversion treatment with zinc phosphate type chemical, Palbond 100 (Our product) was conducted at 95° C. liquid temperature for 10 min followed by water rinsing and drying. In this way, a zinc phosphate coating of 15g/m² coating weight was obtained. To this material was attached an electrode as shown in FIG. 2. It was used as Sample (1) for determining the humidity sensing property.

EXAMPLE 2

The same substrate as in Example 1 was degreased, water-rinsed, pickled, and water-rinsed, in the same way as in Example 1.

Thereafter, conversion coating was applied thereto with Palfos MIA (Our Product), manganese phosphate type chemical, at 95° C. liquid temperature by dipping for 10 min followed by water rinsing and drying. Thus a phosphate coating of 11g/m² coating weight was obtained. To this material was attached an electrode in the same way as in Example 1 and FIG. 2 and used as Sample (2) for determining the humidity sensing property.

EXAMPLE 3

The same substrate, and in the same way, as in Example 1 was degreased, water rinsed, pickled and water-rinsed. Thereafter, the conversion coating was applied thereto with zinc/calcium phosphate type chemical, Ferri Coat 7 (Our Product) at 90° C. liquid temperature by dipping for 10 min, followed by water rinsing and drying. Thus a phosphate coating of 8g/m² coating weight was obtained. To this material was attached an electrode in the same way as in Example 1 and FIG. 2. It was used as Sample (3) for determining the humidity sensing performance.

EXAMPLE 4

Stainless steel (SUS 304) of 0.3mm thickness was degreased and water-rinsed in the same way as in Example 1. It was then pickled with a mixed liquid of 2g/l nitric acid and 15g/l hydrofluoric acid by dipping thereinto for 1 min at 25° C. liquid temperature and then water rinsed. Thereafter, Palbond 100(Our Product), a zinc phosphate type conversion chemical was applied with cathodic electrolysis of 2A/dm² current density for 4 min at 50° C. The work was water rinsed and dried. The coating is weight was 12g/m².

To this material was attached an electrode as shown in Example 1 and FIG. 2. It was used as Sample (4) for measuring the humidity sensing property.

The results of measurements conducted on Samples (1)-(4) thus prepared are described hereunder.

Table 1 indicates the principal coating composition and coating thickness.

Figure 3:
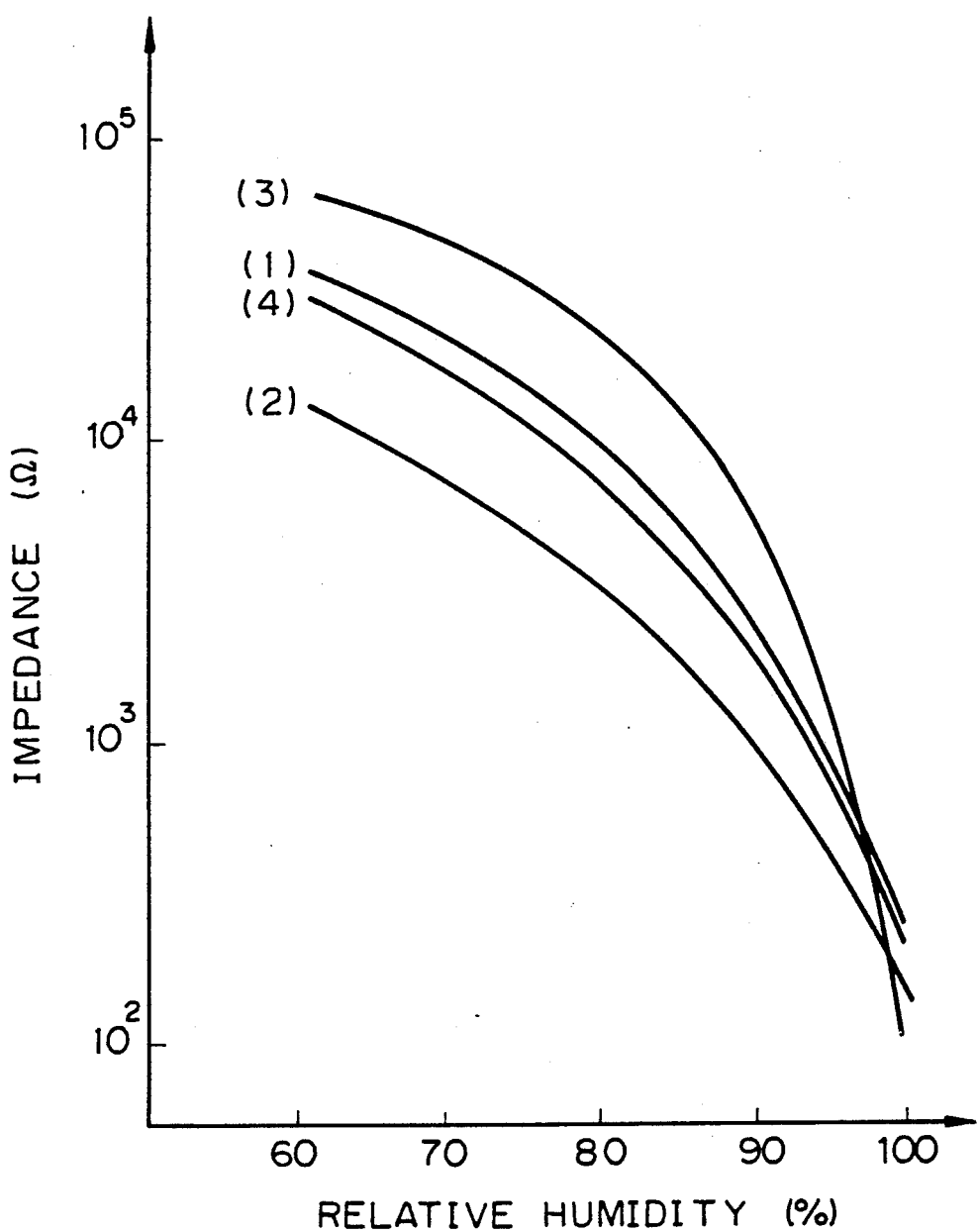
FIG. 3 is the relation between relative humidity and the impedance in the case of samples in the Examples 1-4, which were measured by charging alternating voltage at the humidity sensible element of the sensor (hereinafter referred to as the "humidity sensing characteristic figure").

FIG. 3 indicates the humidity sensing property respectively obtained on the Samples in Examples 1-4, in terms of impedance measured in thermostat at 1 KHz frequency under 0.5V charged voltage.

Figure 4:
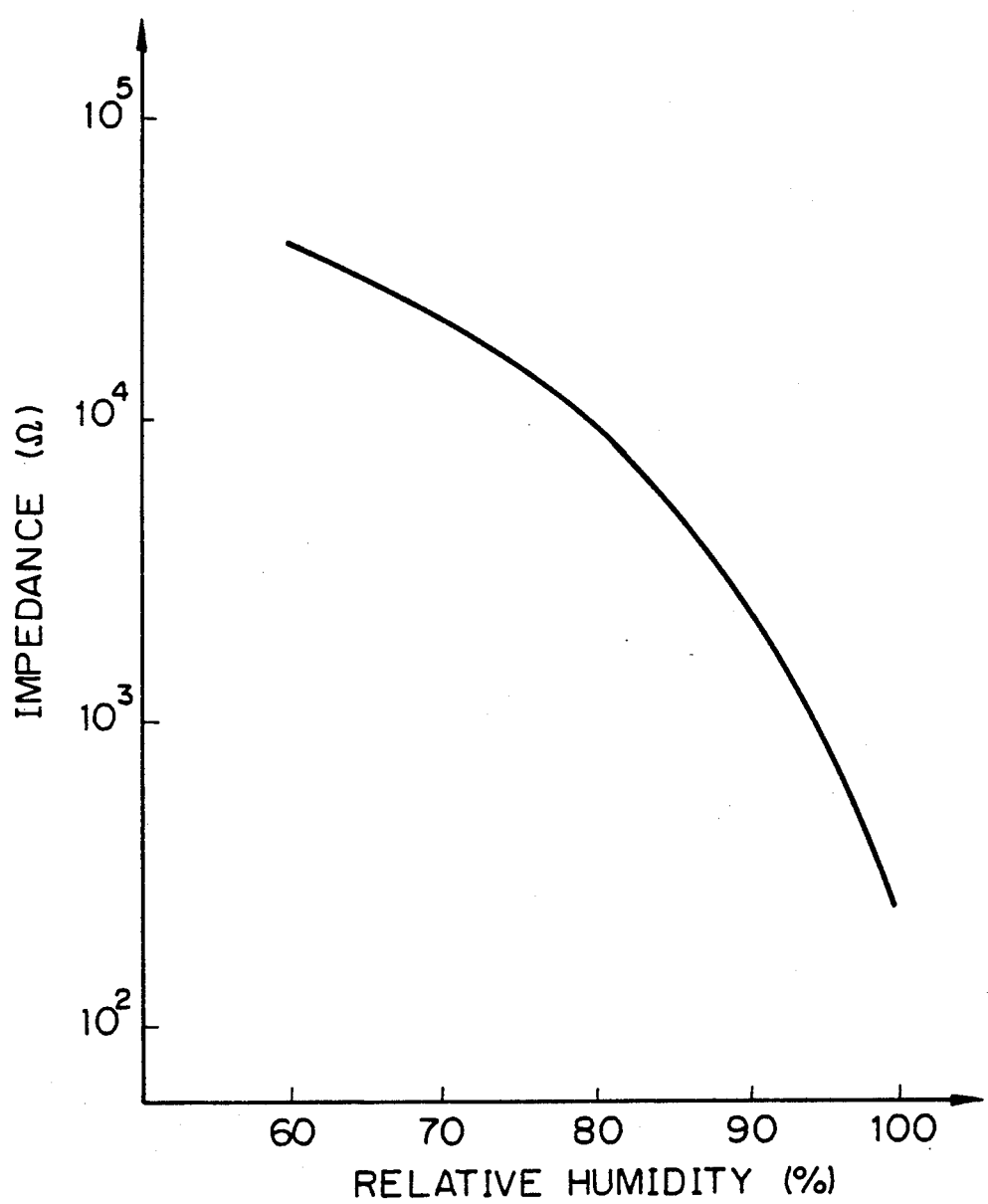
FIG. 4 is the humidity sensing characteristic figure when the sample in Example 1 was left standing at ambient temperature/humidity for 2,000 hr.

FIG. 4 indicates the humidity sensing property of Sample 1 after having been left standing indoors at an ambient temperature and humidity for 2,000hr. As can be seen therefrom, the humidity sensing property receives practically no change and the performance was acknowledged to be of extremely high stability.

Though not indicated in the figures, results of determination obtained on Examples 2-4, indicate that again there was almost no change seen in the humidity sensing performance after 2,000 hr.

TABLE 1

| Sample | Main Composition | Film Thickness (Average) |
|---|---|---|
| Example 1 | $Zn_3(PO_4)_2 \cdot 4H_2O$(Hopeite) $Zn_2Fe(PO_4)_2 \cdot 4H_2O$(Phosphophyllite) | 12 μm |
| Example 2 | $(Mn,Fe)_5 H_2(PO_4)_4 \cdot 4H_2O$ (Hureaulite) | 9.5 μm |
| Example 3 | $Zn_2Ca(PO_4)_2 \cdot 2H_2O$(Scholzite) $Zn_3(PO_4)_2 \cdot 4H_2O$(Hopeite) | 7 μm |
| Example 4 | $Zn_3(PO_4)_2 \cdot 4H_2O$(Hopeite) | 10 μm |

EXAMPLE 5

Figure 5:
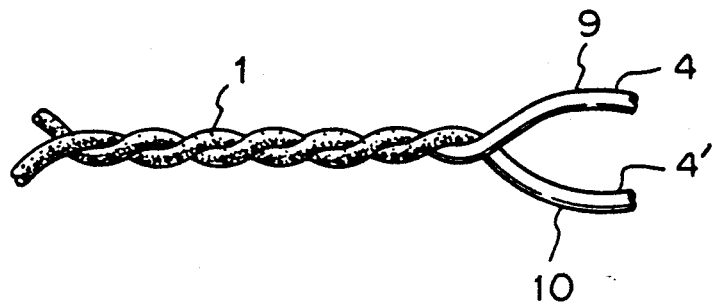
FIG. 5 indicates plans of the humidity sensor element to be applied to Example 5, and examples of structures of humidity sensors to be applied to Examples 9–13.
Figure 6:
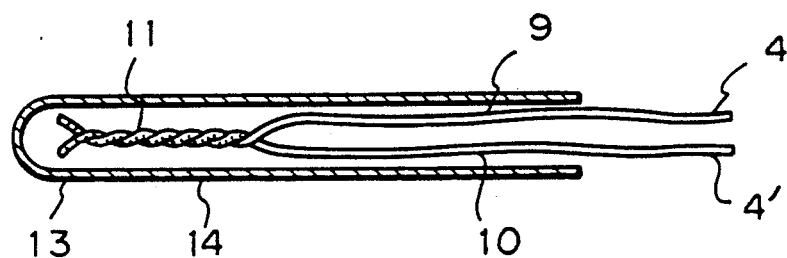
FIG. 6 is the cross-sectional view of the humidity sensor in Example 5.

Examples of the humidity sensor structure provided with a humidity sensing element manufactured by forming a phosphate conversion coating on a copper-based material are indicated in FIG. 5, and FIG. 6. In FIG. 5, 1 is the humidity sensing element, 4 and 4' are lead wires which respectively consist of a spirally formed portion of two copper wires and other portions. One of the two copper wires treated with conversion coating is represented by the metal electrode 9 and the other is the opposite electrode (10). Further, a protecting cover is provided, as shown in FIG. 6. In FIG. 6 those parts marked with the same numerical symbols are respectively of the same structure as in FIG. 5. The numeral 13 stands for a tubular cover which is closed at one end and into which an element as indicated in FIG. 5 is inserted. Of this cover 13, a portion located opposite the humidity sensing element 1 is provided with ventilation openings.

In this Example, the chemical conversion coating was obtained with the following process sequence. Two units of 0.2mmφcopper wire, JIS-H-3260 1100W-0, were treated in the following way.
1) Pickling: dipping in an aqueous liquid containing 1% ferric chloride at ambient for 1 min.
2) Water rinse: with running water
3) Degreasing: dipping in 20g/l INCLENER 4360 (Our Product) at 60° C. liquid temperature for 3 min.
4) Water rinse: with running water
5) Surface conditioning: dipping in 3g/l PREPALEN Z (Our Product, colloidal titanium compound-based surface conditioner)
6) Conversion coating: dipping in 60g/l BLASB0ND K (Our Product) at a liquid temperature from 50° to 60° C. for 5 to 10 min.
7) Water rinsing: with running water
8) Deionized water rinse: flushing
9) Drying: at 100° C. for 3 min.

The coating thus obtained was of 20-25g/l coating weight, comprising Hopeite $[Zn_3(PO_4)_2 \cdot 4H_2O]$ according to X-ray diffraction analysis.

These copper wires, except their end portions, were twisted together as shown in FIG. 5 and again treated with this conversion coating. Thus a humidity sensing element (a) was obtained. This element (a) was dipped for a few minutes in a sodium metaphosphate solution, and a secondary element (b) was obtained. These elements (a) and (b) were provided with a cover as shown in FIG. 6 and they were used as Samples (5a) and (5b) for testing humidity-sensing properties.

Here, it is evident that the interelectrode distance is twice the thickness of the conversion coating. In fact, this was 10 μ to 100 μ according to the determination of interelectrode distance on a few pieces of trial-manufactured articles. Such figures are smaller than seen on conventional humidity sensors. Consequently the resistance was reduced and a humidity sensor having higher sensitivity and response speed could be obtained.

Figure 7:
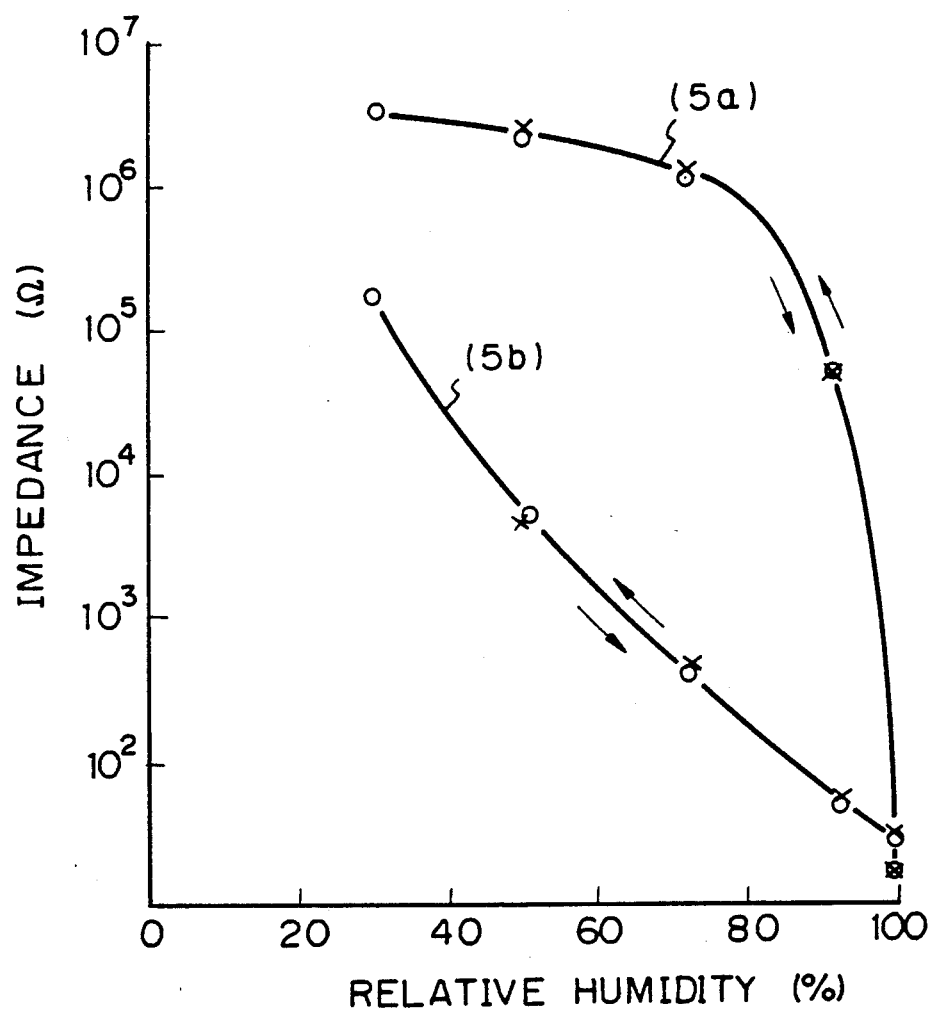
FIG. 7 is the humidity sensing characteristic figure for Example 5.

These humidity sensors 5a and 5b were charged with 0.5V/1KHz alternating voltage. FIG. 7 indicates the relationship between impedance and relative humidity thereby obtained. It is seen therefrom that 5a has good quality as the element for the humidity sensor, and 5b for the dew sensor. To explain further, (5a) in FIG. 7 is the curve for the elements 5a and (5b) showing that there is no difference at all between the cases of humidifying and desiccating. That is, no hysteresis takes place there. This property makes this an element an excellent practical applicant as a dew sensor.

Figure 27:
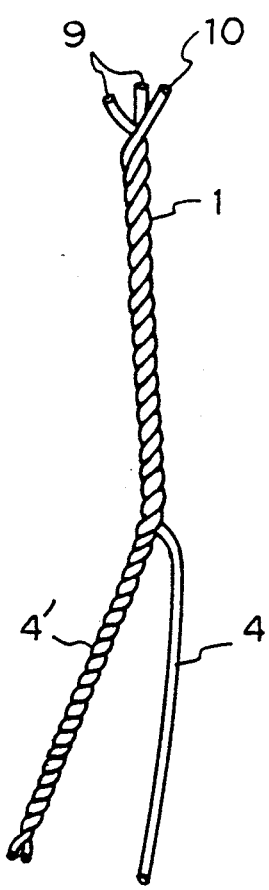
FIG. 27 is a schematic view that indicates an example of the construction of the humidity sensor to be applied to the sample in Example 18.

As shown in FIG. 27 for the structure of the humidity sensor, the wire to be coated with humidity sensing element 1 is not restricted to one in number. It is also possible for the structure of the humidity sensor to take two or more pieces of wire which are twisted together and divided into two groups comprising single or plural wires which, at the end portions, are cut to an adequate length for using the one group as the metal electrode and the other group as the opposite electrode.

In regard to the phosphate coating thickness, 0.5 to 120 $\mu$ is preferable. In the case where the metal electrode or the is opposite electrode is of wire shape and twisted-together or of wound-around structure, a thickness of 0.5 to 30 $\mu$ is more preferable. The reason for this is that a thickness less than 0.5 $\mu$ might cause the film to lose its continuity when two electrodes are brought into contact, resulting in an exposed electrode at some portions wherefrom a short circuit might take place. On the other hand, in the case of more than 120 $\mu$, the surface roughness becomes greater and the contact between the humidity sensor element and the opposite electrode becomes less effective. As a result the interelectrode resistance increases.

Further, in the case of a twisted structure, a film thickness exceeding 30 $\mu$ is subject to delamination/disconnection from the substrate wire.

EXAMPLE 6

Figure 8:
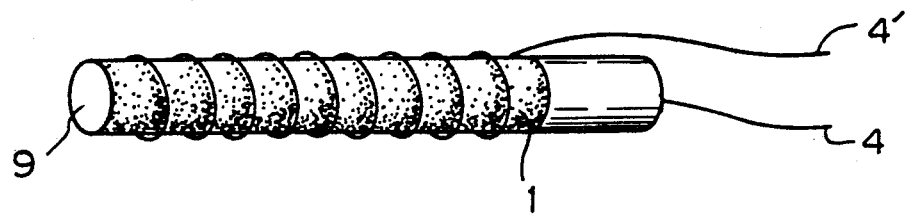
FIG. 8 is the schematic view showing an example of a structure of a humidity sensor to be applied to samples 6–8.

FIG. 8 indicates an example of structure for the humidity sensor having oxalate coating or titanium fluorocomplex salt coating as the humidity sensing element, wherein a cylinder-shape metal 9 treated with said conversion coating to form humidity sensing element 1 is peeled-off therefrom at the one end to use this portion as Electrode 4. Meanwhile, the remaining portion, which is wound around with copper wire, gold plated wire or the like, over the humidity sensing element 1 is used as the opposite electrode.

In this case, stainless wire (0.9 mm$\phi$), SUS 304, JIS-G-4309 was used as the substrate. It was, at first, degreased with Fine Cleaner 4360 (Our Product) by dipping in 2% aqueous liquid at 70° C. liquid temperature for 5 min. After water rinsing, Ferrbond A (Our Product), an oxalate coating chemical was applied thereto by dipping for 10 min at 95° C. liquid temperature, then water rinsing and drying followed. The oxalate coating thus obtained was 10g/m$^2$. This coating was which for the electrode assembly as shown in FIG. 8 as Sample (6) for determining the humidity sensing property.

EXAMPLE 7

Pure titanium wire (0.9 mm$\phi$), JIS-H-4670 was used as the substrate. It was first degreased with Fine Cleaner 315 (Our Product) by dipping into 2% aqueous liquid at 70° C. liquid temperature for 5 min. After water rinsed, it was pickled with a mixed liquid of 20g/l nitric acid and 15g/l hydrofluoric acid by dipping at 25° C. liquid temperature for 1 min then water rinsed. Thereafter Balmet 3851 (Our Product), a titanic acid conversion coating chemical, was used for the conversion by dipping at 65° C. liquid temperature for 1 min, then water rinsing and drying followed. The coating weight of titanium fluorocomplex salt thus obtained was 10g/m$^2$. According to the chemical analysis, this coating was 44.5% in F, 26.0% in Na and 24.6% in Ti. The X-ray difraction analysis indicated $Na_3TiF_6$ for the composition. This coating was assembled with the electrode as indicated in FIG. 8 and used as Sample (7) for measuring the humidity sensing property.

EXAMPLE 8

A titanium fluorocomplex salt coating as in Example 7 was dipped in an aqueous liquid of 10% sodium metaphosphate at 20° C. for 1 min and a coating having sodium metaphosphate retained therein was obtained. To this coating was attached an electrode as indicated in FIG. 8 and used as Sample (8) for measuring the humidity sensing property.

In regard to the oxalate coating and titanium fluorocomplex salt coating, further explanation will be made hereunder with regard to Examples 6 to 8.

Figure 9:
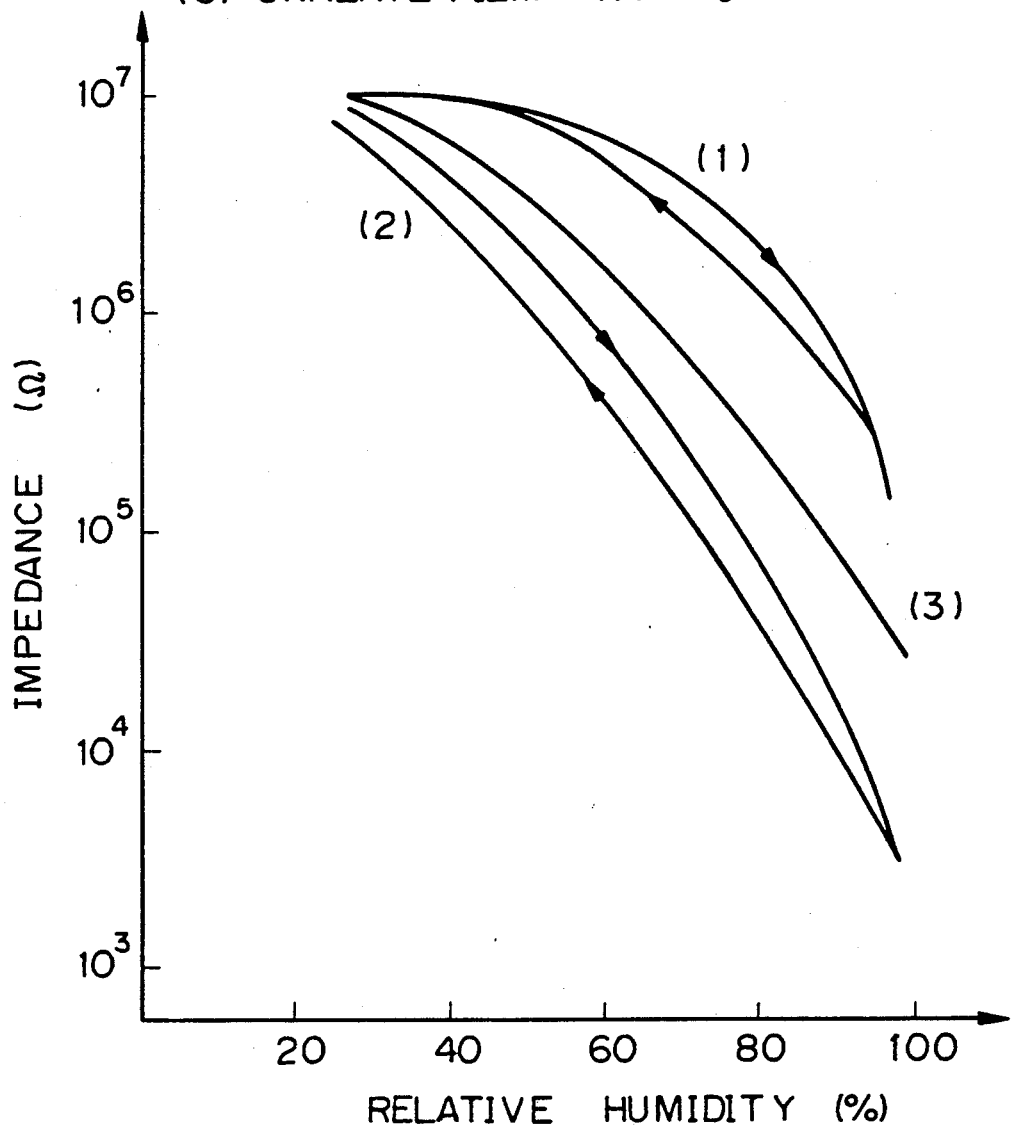
FIG. 9 is the humidity sensing characteristic figure obtained by taking measurements on samples using Examples 6–8.

FIG. 9 indicates the results of determination of the humidity sensing property with respect to samples in Examples 6 to 8. In this case, impedance was used as the parameter, whose measurement was conducted at 25° C. by charging 1KHz 0.5V. The figure is plotted with impedance as abscissa and relative humidity as ordinate.

As FIG. 9 (1) indicates, oxalate coating yields steep reduction of impedance when relative humidity exceeds 75%. This is a property suitable for a dew-type sensor.

This oxalate coating, when post-treated to make sodium metaphosphate retained therein, is converted to a humidity type as shown in FIG. 9 (3).

In the case of titanium fluorocomplex coating which is indicated in FIG. 9 (2), a correlation between humidity in the range of 30 to 100% and impedance is observed. This is a humidity-type property.

Figure 10:
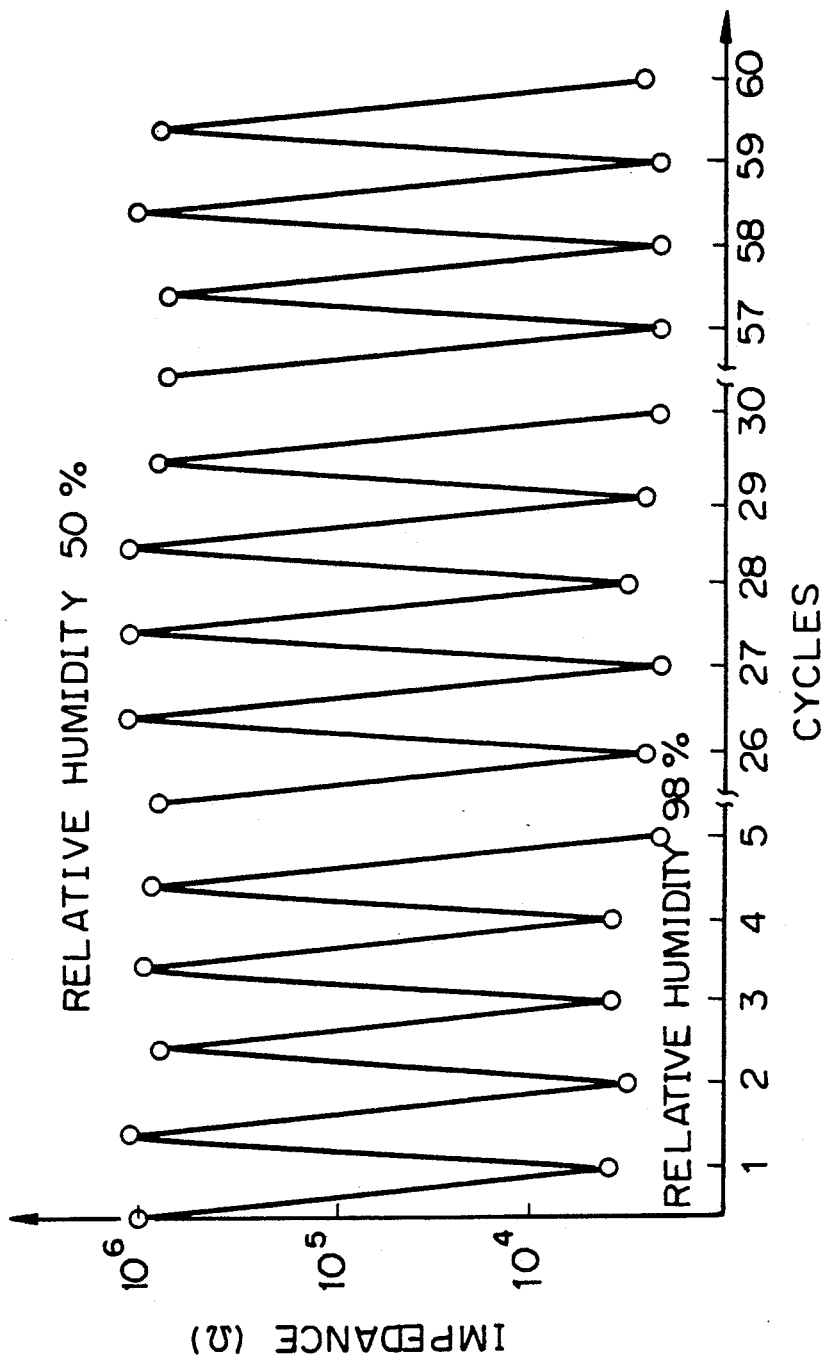
FIG. 10 is the humidity sensing characteristic figure that indicates the durability of titanium fluorocomplex salt coating.

FIG. 10 is for the humidity sensing property in terms of durability, in the case where titanium fluorocomplex coating in Example 7 is used as a humidity sensor element: This sensor was subjected to cyclic change of relative humidity, in the manner of 98%→50%→98%→50%→ and determination of impedance was conducted respectively.

The result, as shown in that figure, indicates that, even after 60 cycles the property is held constant. This verifies the good durability of this sensor.

Figure 11:
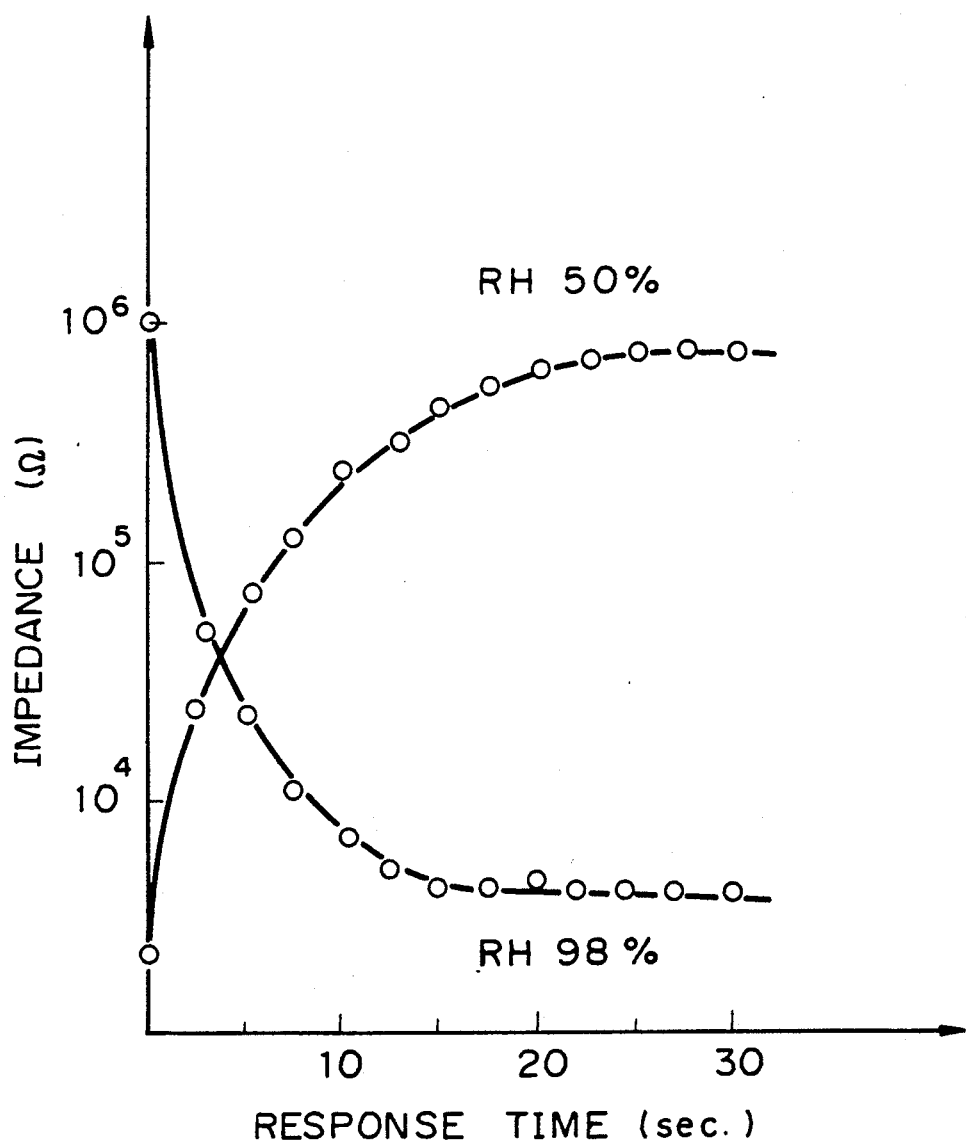
FIG. 11 is the humidity sensing characteristic figure that indicates the response time of titanium fluoro complex salt coating.

FIG. 11 is for the humidity sensing property of titanium fluorocomplex salt coating in Example 7 in terms of response time to humidity. It is seen therefrom that response time is 10 sec in the case of humidifying, and 20 sec in the case of desiccation, quicker than that of conventional products, (available on market). This advantage is due to the fact that the electrode distance is as small as 10 to 20 $\mu$ between the metal electrode and the opposite electrode.

EXAMPLE 9

For the structure of the humIdity sensor usIng chromate coating or non-chromate coating as the humidity sensor element, the same one as in FIG. 5 was used.

Aluminum wire (0.3mm$\phi$), JIS-H-4040 A1070W-0 was used as the substrate. It was first degreased with Palclean 450 (Our Product: hereinafter referred to as CL450) by dipping into 3% aqueous liquid at 60° C. liquid temperature for 1 min. After water-rinsed, it was treated with Alchrom 701 (Our Product) by dipping at 70° C. liquid temperature for 5 min and water rinsing and drying followed. The coating thus obtained was of 1000g/m$^2$ of chromium in the coating. This coating was assembled with an electrode as indicated in FIG. 5 and used as Sample (9) for measuring the humidity sensing property.

EXAMPLE 10

Aluminum wire (0.3 mm$\phi$), JIS-H-4040 A1070W-0 was first degreased with CL450 (Our Product) by dipping in 3% aqueous liquid at 60° C. liquid temperature for 1 min. After water rinsing, conversion coating was effected with palcoat 3751 (Our Product), a non-chromate conversion coating chemical, by dipping at 70° C. liquid temperature for 5 min. then water rinsing and drying followed. Thus a coating of titanium-tannic acid complex salt, having 50mg/m$^2$ of titanium in the coating, was obtained. This coating was assembled with an electrode as indicated in FIG. 5 and used as Sample (10) for measuring the humidity sensing property.

EXAMPLE 11

Aluminum wire (0.3 mm$\phi$), JIS-H-4040 A1070W-0 was first degreased with CL 450 (Our product) by dipping in 3% aqueous liquid at 60° C. liquid temperature for 1 min. After water-rinsed, it was conversion-treated with palcoat 3753T (Our Product), a non-chromate conversion treatment chemical, by dipping for 5 min then water-rinsed and dried. Thus a coating of zirconium-phytic complex salt having 50mg/m$^2$ of zirconium in the coating was obtained. This coating was assembled with an electrode as indicated in FIG. 5 and used as Sample (11) for measuring the humidity sensing property.

EXAMPLE 12

Aluminum wire (0.3mm$\phi$), JIS-H-4040 A1070W-0 was first degreased with CL 450 (Our Product) by dipping in 3% aqueous liquid at 60° C. liquid temperature for 1 min. After water rinsing, a roll-on type chromate conversion treatment chemical, Zinchrom R 1415 A (Our Product), was applied by dipping at 70° C. liquid temperature for 5 min then water rinsing/drying was effected, whereby a roll-on type chromate coating having 100mg/m$^2$ chromium therein was obtained. This coating was assembled with an electrode as indicated in FIG. 5 and used as Sample (12) for measuring the humidity sensing property.

EXAMPLE 13

Chromium phosphate coating as in Example 9 was treated further with 10% aqueous liquid of sodium metaphosphate by dipping at 20° C. for 1 min so as to retain therein sodium metaphosphate. This coating was assembled with an electrode as shown in FIG. 5, and used as Sample (13) for measuring the humidity sensing property.

Figure 12:
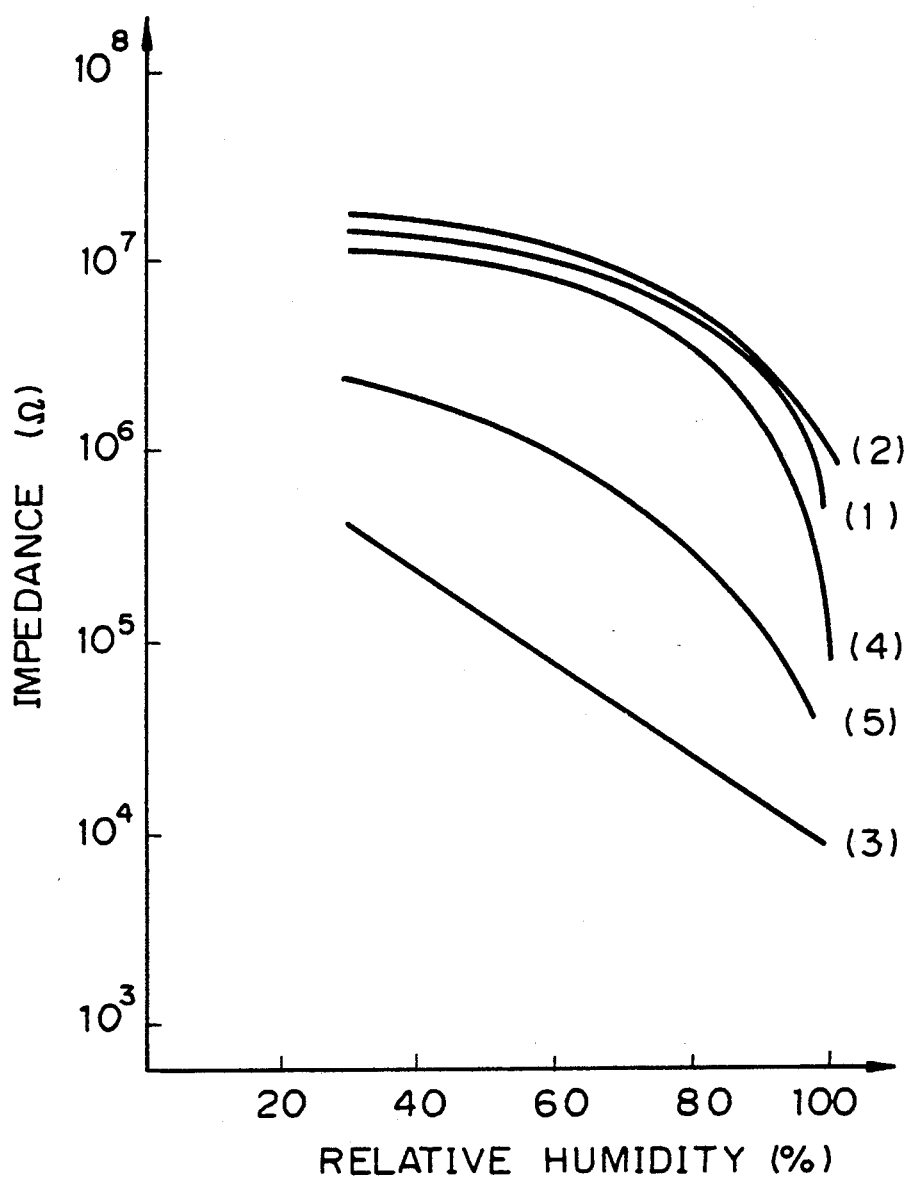
FIG. 12 is the humidity sensing characteristic figure obtained by taking measurements on the samples in Examples 9–13.

As for Examples 9-13, the results obtained on respective Samples for the humidity sensing property are shown in FIG. 12. In this figure, the ordinate shows the impedance $\Omega$) determined at 20° C. under charged voltage of 0.5V, 1KHz frequency, and the abscissa, the relative humidity.

As seen from (1) in this figure, the chromium phosphate coating indicates a steep reduction of impedance at the proximity of 100% relative humidity. This is a typical property required for a dew type sensor.

When such a chromium phosphate coating is post-treated to retain therein sodium metaphosphate, it is converted to humidity type one as shown in (5) of this figure.

As for the titanium-tannic acid complex salt coating and the roll-on type chromate coating respectively shown as (2) and (4) in FIG. 12, these two coatings both indicate steep decreases in their impedances at 75 to 100% relative humidity, showing that they have a dew-type sensor property.

As to the zirconium-phytic acid complex salt coating shown as (3) in this figure, a linear relationship holds true between relative humidity in the 30 to 100% range and the logarithm of impedance. This is a typical property for humidity type sensor.

Figure 13:
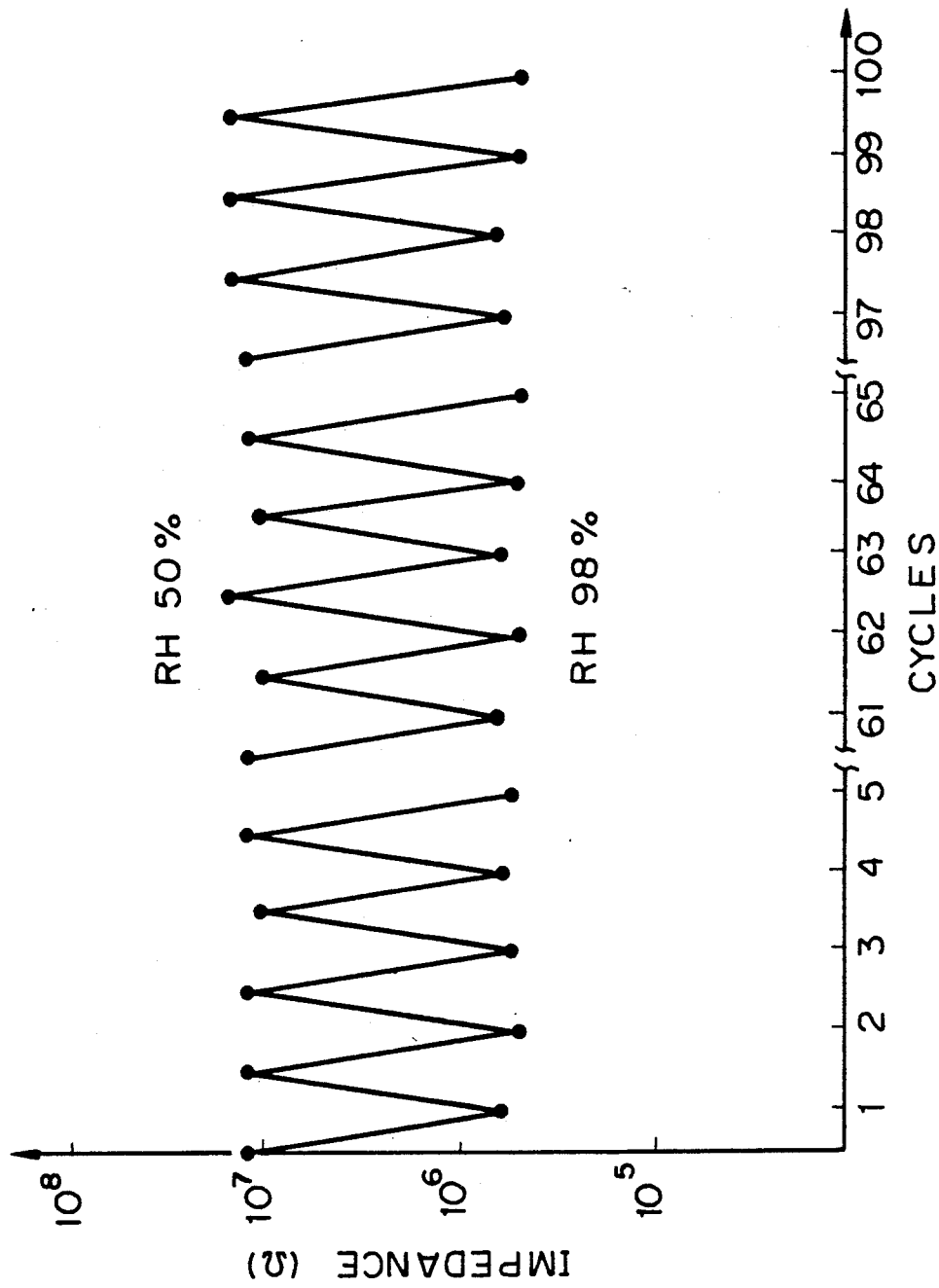
FIG. 13 is the humidity sensing characteristic figure indicating the durability of chromium phosphate coating.

FIG. 13 corresponds to the case where the chromium phosphate coating of Example 9 used as the humidity sensor element, was subjected to cyclic change in relative humidity, 98% →50%→98%→50%, and, at that time, change of impedance was measured. The result was that even after a 100-cycle test, the value was of stable reproducibility, verifying its durability as a humidity sensor.

Figure 14:
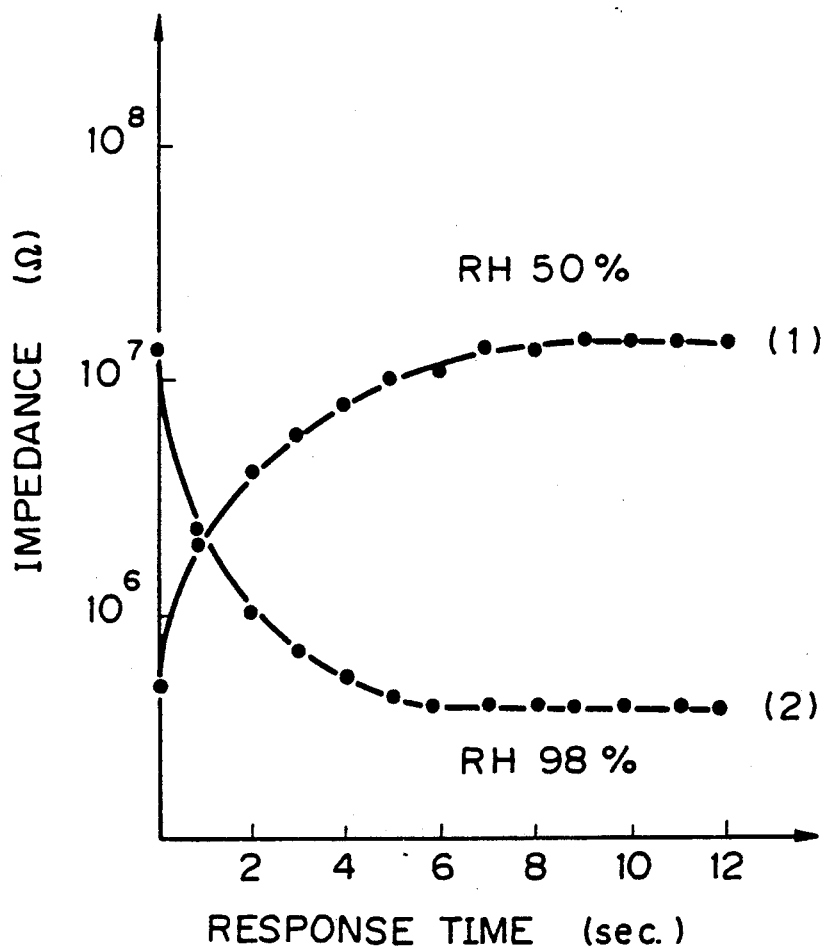
FIG. 14 is the humidity sensing characteristic figure indicating the response time of chromium phosphate coating.

FIG. 14 indicates the result of determination of the chromium phosphate coating of Example 9 for the response speed to humidity. It indicates 5 sec in the case of humidifying and 10 sec in the case of desiccating, which are both quicker than those given by humidity sensors available on the market. Such high speed response is due to the electrode distance between the metal electrode and the opposite electrode being as small as 0.5 to 5 $\mu$.

Next, an explanation will be given on Examples 14-17, where the humidity sensors use humidity sensing film coated on conversion treatment coating.

EXAMPLE 14

FIG. 15 indicates a practical example of this invention to show the structure of the humidity sensor. FIG. 15A is the schematic view and FIG. 15B the longitudinal section of the electrode terminal portion under magnification.

Using the metal electrode 9 as the No. 1 electrode, stainless wire 14 (SUS 304) is used, in which a zinc phosphate type humidity sensing element 1: $Zn_3(PO_4)_2 \cdot 4H_2O$ (Hopeite), is coated by the electrolytic conversion process. On the coating 1 is formed the humidity sensing film 13 to the surface of which is attached the opposite electrode 10 as the No. 2 electrode. The opposite electrode is wound around with gold-plated stainless wire of 0.13 mm$\phi$ with a 0.5 mm interval in coil spacing.

At both ends, a fixer (22) is provided to prevent the electrode from getting loose. Note here that No. 2 electrode is not restricted to being a metal electrode: any material, provided that it is electroconductive and of wire shape, is applicable, for the electrode construction; carbon fiber, high molecular conductive material etc.

The terminal of each electrode, 4 and 4', is connected with a lead wire to out-side circuit (not illustrated).

The coating of humidity sensing element film to a metal electrode is effected in the following way.

First, stainless wire is degreased with Fine Cleaner 4303 (Our product) by dipping into 20g/l aqueous liquid for 3 min. After cleaning with running water, it is dipped in an aqueous mixture of 15g/l hydrofluoric acid and 20g/l nitric acid at ambient for 3 min to pickle/clean the surface.

After water rinsing again, it is electrolytically conversion-treated with a liquid having a composition of $Zn^{+2}$ 6.15g/l, $PO_4^{-3}$ 5.6g/l, $NO_3^{-1}$ 9/9g/l and $NaNO_3$ 10g/l at 55° C.

This electrolytic conversion treatment was done by setting stainless wire as the anode and a graphite sheet as the cathode and passing electricity at 1A for 3 min. It is then followed by reversing the electrode poles and applying thereto 0.2A×3 min of reverse electricity. After that, full water rinse is o effected, then drying-off at 100° C. for 5 min is conducted. The coating thickness of the conversion treated humidity sensing element thus obtained is 13 $\mu$. For the determination of impedance of this humidity sensing coating, attention is paid not to mar its surface; This is done by catching the metal electrode 9 with the determination terminal 15 as illustrated in FIG. 16, and alternating current resistance 16 is used to determine the resistance of the coating between the measurement terminal and the electrode with respect to various points of coating. The result obtained is 20 to 200$\Omega$. This means that is the coating was electroconductive without having a humidity sensing function.

The humidity sensing film coated on the humidity sensing coating 1 is formed by means of applying a paste which was prepared as follows: zinc phosphate powder $Zn_3(PO_4)_2 \cdot 4H_2O$ was added to thermoreaction type watersoluble resin (ELASTRON H.38, product of DAIICHI KOGYO SEIYAKU: hereinafter referred to as H.38) in proportion of 10g for the former to 8ml for the latter; it was kneaded with the addition of water and the viscosity was adjusted so that a thread could be produced. FIG. 17 indicates the longitudinal cut-section: the metal electrode 9 coated with the humidity sensing element film 1 is inserted into the paste 17 in the paste holder 18, passed through the nozzle hole 20 of nozzle 19, and drawn down in the direction of the arrow; that is, when passing through the paste holder, the surface of the humidity sensing film becomes wet with paste, the amount of deposit is controlled by the nozzle hole size, and the coating 13 is formed with uniform thickness.

Since the removable nozzle 19 is designed to allow the use of metal electrode cylinders of different dimensions, the thickness of the coating layer is also variable. In this Example, a nozzle with a hole of 9.05 mm hole was used. The electrode wire with the coated layer was left standing in the air for 10 hr, then placed into an oven at 160° C. for 5 min to solidify the paste. Thus a metal electrode having a humidity sensing film of 11 $\mu$ thickness was obtained.

In place of air drying for paste film, oven heating is applicable as a matter of course. However, as rapid heating might cause steam to suddenly generate in a large quantity, resulting in destruction of the coating film, heating at below 100° C. is desirable.

The solidified coating obtained through drying and heating at 160° C., is a coating on a humidity sensing element obtained by conversion coating, distributed with in numerous fine pores. These pores play role of footholds for the paste adhesion, an anchoring effect, owing to which the solidified film can get rid of any risk of being detached from the underlying Hopeite coating. Further, as the primary constituent of the coating is zinc phosphate, $Zn_3(PO_4)_2 \cdot 4H_2O$, as the primary constituent which is slightly soluble in water dissociating into ions, and, the water is gone, loses its conductivity, the coating film, when it is less than 20 $\mu$ in thickness, varies greatly in response to the magnitude of humidity increase/decrease. This is excellent sensitivity for humidity. That is, in the case of this invention with the metal electrode with conversion coating and 11 $\mu$ of the abovementioned film, the state of current continuity observed in the metal electrode with conversion coating alone as the humidity sensing film, was repaired by said post treatment of 11 $\mu$ thickness in order to get more than 1 M $\Omega$ impedance at 50% relative humidity (hereinafter referred to as RH), indicating the recovery of the humidity sensing function.

However, in case it exceeds 2 $\mu$ in thickness, the influence of electric insulation provided by the resin as a coating constituent becomes stronger and it takes longer for humidity to penetrate thereinto. Consequently even at higher humidity, reduction of impedance is minor, and the humidity sensing function tends to become degraded.

The reason why stainless wire with gold plating is used or the opposite electrode which is wound around on its humidity sensing coating is to minimize the contact resistance between the coating film layer and the electrode. Provided this condition is satisfied, no restriction is given in this invention In the case where a corrosive environment should be taken into account, nickel plating or platinum plating is also effective.

In order to prevent the coil-form-wound opposite electrode from losing its tightness by a spring-back effect, an epoxy-type adhesive (Product of KONISHI Co., Ltd.: hereinafter referred to as "adhesive") fixer 22 is used to adhesion-fix the metal electrode at the spiral portion across is several pitches. It is also possible to use Nylon thread or fine metal wire to fasten such a portion and then fix it with resin.

The electric resistance changes in response to the amount of moisture in the humidity sensing element and humidity sensing coating film. Thus, by connecting the lead wire of the electrode to an outside electric resistance measurement apparatus, interelectrode impedance is read out to determine the humidity.

The humidity sensing element 1 consisting of a phosphate coating and the humidity sensing film 13 having phosphate as the principal constituent, both have a very thin coating of 10 $\mu$ order and consequently the impedance is far smaller than the area resistance obtained by using a conventional comb-shaped electrode.

The reason for using stainless wire of SUS 304 as the electrode 9 in FIG. 15 is that it is suitable for conducting electrolytic conversion coating to enable the phosphate coating to be used as the humidity sensing element. Besides this, iron, copper, nickel and titanium, on which phosphate coating is formable, are available as metal electrodes.

Figure 18:
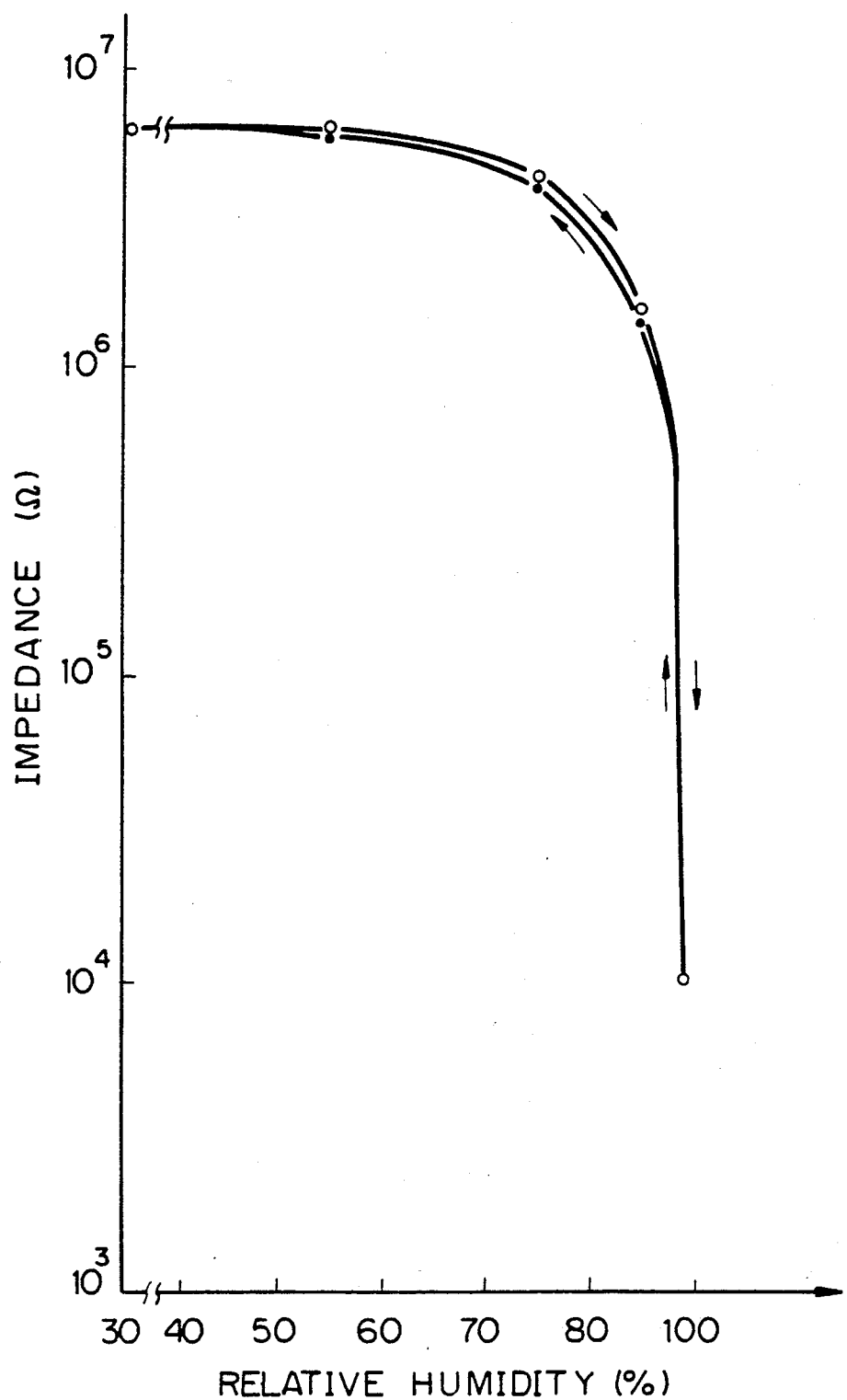
FIG. 18 is to humidity sensing characteristic figure obtained by measuring the sample in Example 14.

FIG. 18 shows an example of such an electrode: the humidity sensing property measured by applying 1KHz 0.5V electric source is plotted semilogarithmically. As seen therefrom in a low humidity range of less than 75% RH, the humidity sensor prepared by forming humidity sensing film 13 on humidity sensing element 1, indicates high impedance not very variable in relation to humidity change. However, in a high humidity range, the impedance varies steeply.

It is also notable that between the cases of humidifying and desiccating, there is almost no difference in impedance at the same humidity. This is a big advantage of this humidity sensor as a dew-type sensor.

This humidity sensor was subjected to the wet/dry cycle test of RH 70% ⟵⟶ 98% 1,000 times. Table 2 indicates the impedance observed during this cycle. From this table, it is seen that the impedance hardly changes at all through the initial period to the end period of the test, and therefore it has excellent stability. In the table, K means dry/wet cycle.

TABLE 2

| K | 1 | 100 | 500 | 1,000 |
|---|---|---|---|---|
| R H 70% | 4.9 MΩ | 4.8 MΩ | 4.85 MΩ | 4.8 MΩ |
| R H 98% | 8.8 KΩ | 8.6 KΩ | 8.8 KΩ | 8.7 KΩ |

In this example, the metal electrode used was cylindrical.

It is a matter of course for the metal electrode to take a plate shape: after coating a humidity sensing element by chemical conversion treatment on both sides, the formation of a humidity sensing film on both sides can lead to low resistance to humidity sensitivity.

EXAMPLE 15

FIG. 15(A,B) is another example of a humidity sensor presented by this invention, showing a humidity sensor prepared by coating a humidity sensing element on a metal electrode over which, further, a humidity sensing film consisting of two layers 13 and 13' is coated.

Figure 19A:
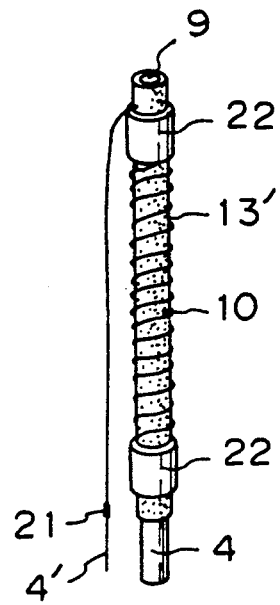
FIG. 19A indicates the appearance of the humidity sensor.
Figure 19B:
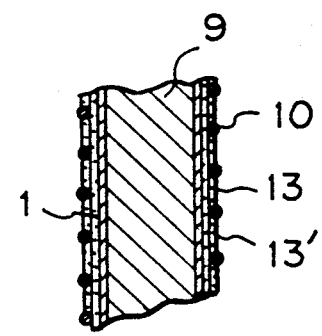
FIG. 19B indicates a part of the sensor under magnification.

This figure is to show the structure; FIG. 19A is a schematic view to show the general appearance; FIG. 19B is a magnified longitudinal section of the humidity sensing portion. For the metal electrode 9 to be used as No. 1 electrode, 0.6mm of copper is used on which is coated the humidity sensing element 1, $Zn_3(PO_4)_2 \cdot 4H_2O$ (Hopeite), by means of conversion treatment. On this coating is formed the humidity sensing film 13. Adjacent to this film is attached the opposite electrode 10 around which nickel wire (50μϕ) gold-plated to 0.5 thickness is wound in coil form at a 3 mm interval. After setting the opposite electrode, the humidity sensing film 13' is further formed on the humidity sensing film 13. Both ends of the wire coiled around the electrode 9 are collected to form wire 21 which is the electrode terminal 4' so that, during humidity measurements the current density can be made uniform between the metal electrode and the opposite electrode over the whole length of the electrode.

The chemical conversion coating of copper was done according to Example 5. The coating thickness obtained was 8 μ. This coating was measured for impedance according to the above-mentioned method. Though the value obtained, more than 1 M was satisfactory, this coating was too thin and was destroyed when the opposite electrode wire was wound around it; as a result electric continuity was took place with loss of the humidity sensing function.

As to the humidity sensing film 13 on the humidity sensing element 1, the same method and the same paste as in Example 14 were used for coating, drying and solidifying to form a coating of 9 μ thickness. The formation of this film layer strengthened the underlying humidity sensing element and the risk of circuit continuity, which might otherwise come from winding opposite electrode wire around it, disappeared.

In winding up electrode wire, the initial and final portions were fixed to the film with an adhesive (ALLON α product of TOAGOSEI Chemical) to prevent the electrode from springing back and unwinding. After fixing the electrode, the humidity sensing film 13' was formed on the humidity sensing film 13 wherein a paste prepared by kneading a mixture comprising 45g $Zn_3(PO_4)_2 \cdot 4H_2O$ . $0.9gK_4P_2O_7$, 3.1ml sodium metaphosphate aqueous liquid and 3.0 ml H-38 was applied in same way as abovementioned. The film, after being subjected to drying in an 80° C. oven for 20 min, was heated up to 160° C. for 5 min and solidified. As for the thickness of this humidity sensing film, enough to bury the opposite electrode in the film layer is desirable. In case it is so thick that the entire wire is buried in, the speed for detecting humidity is slowed down.

Figure 20:
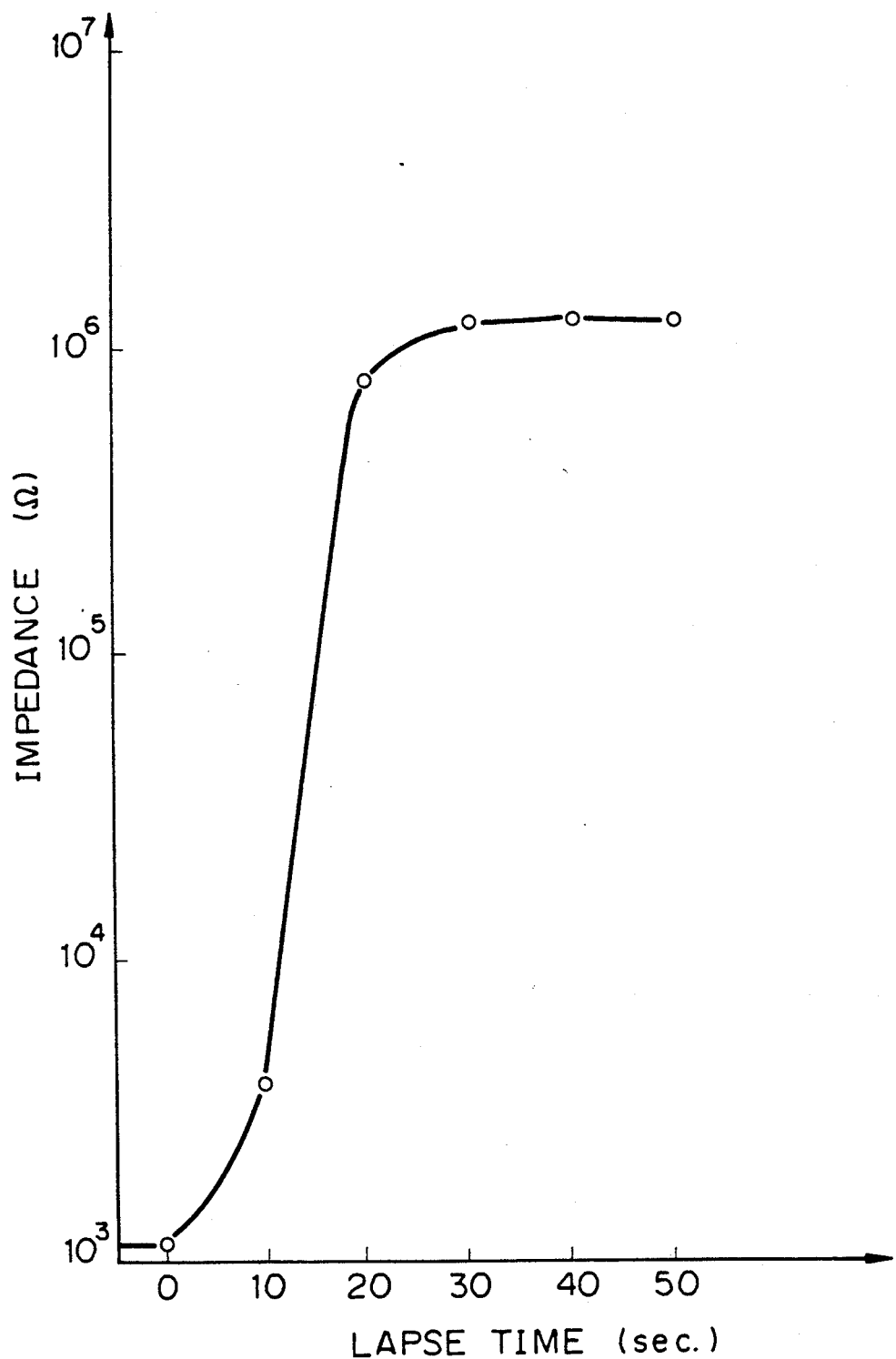

The thickness of this film is controllable by changing the amount of water in the paste, that is, by varying the proportion between the aquenous liquid of sodium metaphosphate and $Zn(PO_4)_2 \cdot 4H_{20}$ used for the preparation of the paste. The thickness in this Example was 21 μ. This sensor was held in an atmosphere of 98% humidity for 24hr, then transferred to an atmosphere of 30% RH. FIG. 20 indicates the impedance variation in this case.

The impedance increases from around 1KΩ at 98% RH to 1MΩ within 20 sec, indicating good property for humidity sensitivity. FIG. 21 is for the relationship between humidity and impedance in this case.

In the process of exchanging RH from 30% to 98% and vice versa, the impedance change in response to humidity change takes the form of a gentle curve. Therefore, the humidity sensing property changes from dew type to humidity type. Furthermore, the two curves in the cases of humidifying and desiccating coincide with each other, without yielding hysteresis.

Table 3 indicates the impedance when "RH 30↔98%" was repeated 1,000 times. (K: humidity cycle No.)

TABLE 3

| K | 1 | 100 | 500 | 1,000 |
|---|---|---|---|---|
| R H 30% | 1.499 MΩ | 1.251 MΩ | 1.251 MΩ | 1.252 MΩ |
| R H 98% | 1.080 kΩ | 1.056 kΩ | 1.060 kΩ | 1.059 kΩ |

As can be seen, impedance is stable with almost no change from the incipient test period to the final stage.

In this way, the humidity sensing property changed from the humidity type to dew type. This is due to the effect of potassium pyrophosphate and sodium metaphosphate, watersoluble alkali phosphate being strongly hygroscopic in nature, which were used as humidity sensing film components. Also, even in as low a range of humidity as 30% RH, the impedance can be held down, as can be seen from the comparison of FIG. 18 with FIG. 21.

Further, the formation of this film layer is effective in making the opposite electrode firmly adhere with the underlaying humidity sensing film layer without yielding any dislodgement between the two. The fact that, even by repeating dry/wet cycle, there was no variation of impedance observed, should be ascribed to this effect.

It is notable here that, though this experiment used a mixture of watersoluble potassium pyrophosphate and sodium metaphosphate as the paste components, usage of either one of them is also possible. Also, a similar effect is obtainable when the humidity sensing film is prepared on a conversion treatment coating made to retain a moisture which is impregnated therethrough. It is also possible to impregnate such an absorbent into the humidity sensing film already prepared.

EXAMPLE 16

Figure 22A:
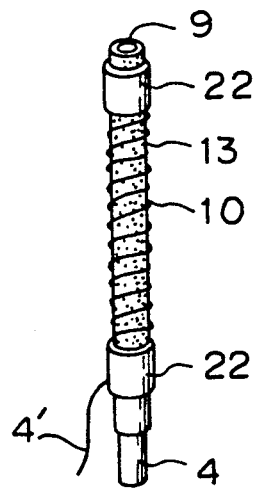
FIG. 22A indicates the appearance of the humidity sensor.
Figure 22B:
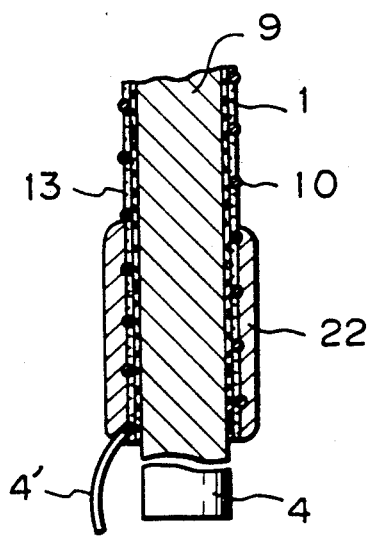
FIG. 22B is a magnified vertical section of part of the sensor.

FIG. 22 (A,B) is the structure of a humidity sensor wherein the humidity sensing film layer was formed on the metal electrode 9 around which the opposite electrode wire was previously wound in contact with the humidity sensing element of conversion coating 1. In this case, the sensing element of the conversion coating was rectified for the defects observed in Examples 14 and 15. In concrete terms, for 0.6 mm φ iron wire was used as the metal electrode 9 and 0.14 mmφ piano wire nickel-plated to 1 μ thickness and gold-plated to 0.5 φ thickness as the opposite electrode; the humidity sensing element was prepared by conversion treatment according to Example 2 so as to form manganese type phosphate coating, (Mn, Fe) $2H_2(PO_4)_4.4H_2O$ (Hureanlite). As the humidity sensing film to be formed on the humidity sensing element, a paste prepared according to the method in Example 14 by using Hureanlite powder, watersoluble epoxy resin KOL EX 313 as binder and EPOMIN (product of NAGASE Chemical Industry) was coated/dried with firm adhesion.

Figure 23:
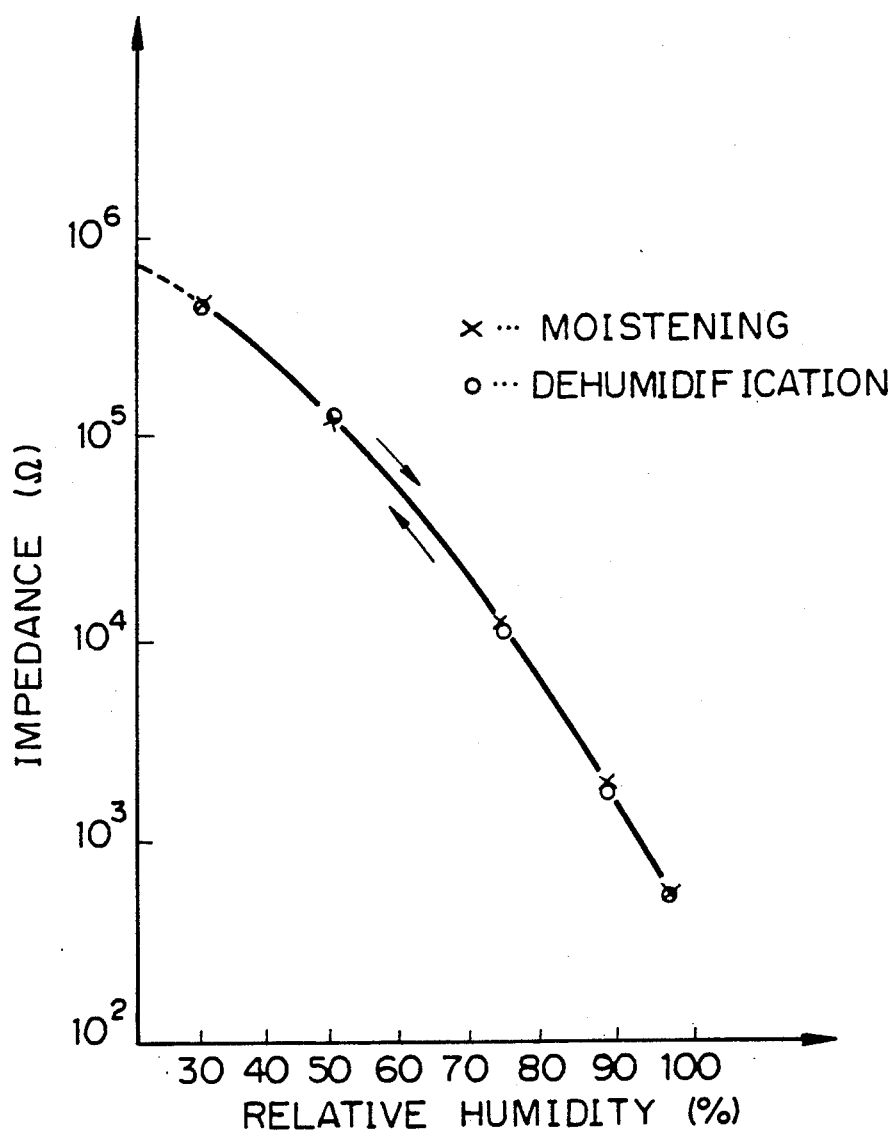
FIG. 23 is the humidity sensing characteristic figure obtained by measuring the samples in Example 15.

FIG. 23 and Table 4 respectively show the impedance characteristics of this example and data of impedance in the case of performing the humidifying/desiccating cycles up to 1000 times.

TABLE 4

| wet/dry cycle | 1 | 100 | 500 | 1000 |
|---|---|---|---|---|
| RH 30% | 340 kΩ | 342 kΩ | 340 kΩ | 341 kΩ |
| RH 98% | 455 Ω | 453 Ω | 450 Ω | 452 Ω |

EXAMPLE 17

FIG. 24 (A-F) shows examples of the humidity sensor produced by this invention, prepared by a coating single wire with a humidity sensing element of conversion coating, over which is formed humidity sensing film layer. FIG. 24A is a case of stainless wire having thereon humidity sensing element coating and humidity sensing film. FIG. 24B is a magnified longitudinal cut section indicating humidity sensing coating/and humidity sensing film layer 13 prepared according to the procedure of Example 14, in the following way.

Figure 24A:
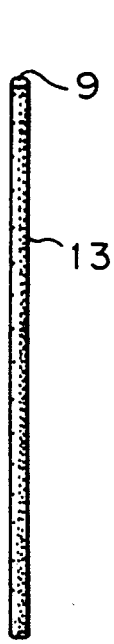
FIG. 24A is the front view of the humidity sensor element.
Figure 24B:
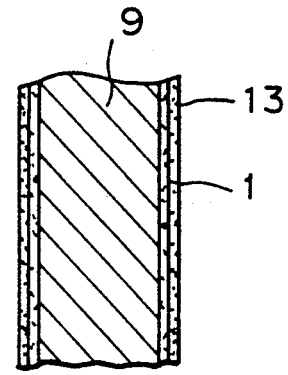
FIG. 24B is a magnified vertical section of part of the sensor.
Figure 24C:
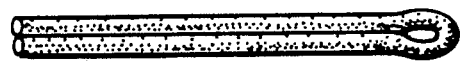
FIG. 24C–FIG. 24E are schematic drawings showing the manufacturing process of the sensor.
Figure 24D:
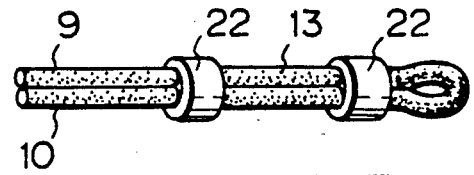
Figure 24E:
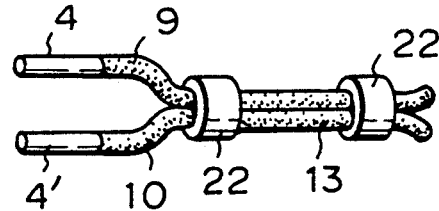

0.3 mmφ stainless wire coated with a humidity sensing element was dipped for 1 min into an acryl-base emulsion containing colloidal silica (trade name. VON-COAT DV 759, product of DAINIPPON Ink Ind., hereinafter referred to as "colloidal silica/acryl composite particle emulsion") then dried at 100° C. for 15 min to form a thin film layer with moisture permeability. FIG. 24 (C.D.) shows schematically the process of assemblying the sensor. As indicated in FIG. 24C, a stainless wire is bent in two to come into contact with each other. Then it is cut at the bent portion as shown in FIG.24E. One wire is used as the metal electrode and the other is used as the opposite electrode. In order to prepare the electrode terminal leads 4 and 4' it is enough to peel off the humidity sensing film layer together with the underlying humidity sensing coating at the electrode terminal portion.

In the case of assembling a humidity sensor conforming to FIG. 24E, the humidity sensing function is as indicated in Table 5 for the relation between humidity and impedance.

TABLE 5

| RH % | 30 | 50 | 75 | 90 | 98 |
|---|---|---|---|---|---|
| Impedance | 20 MΩ | 3.53 MΩ | 136.5* | 12.38* | 3.48* |

Note: Test condition: 1 KHz, 0.5 V
*indicates KΩ

Figure 25:
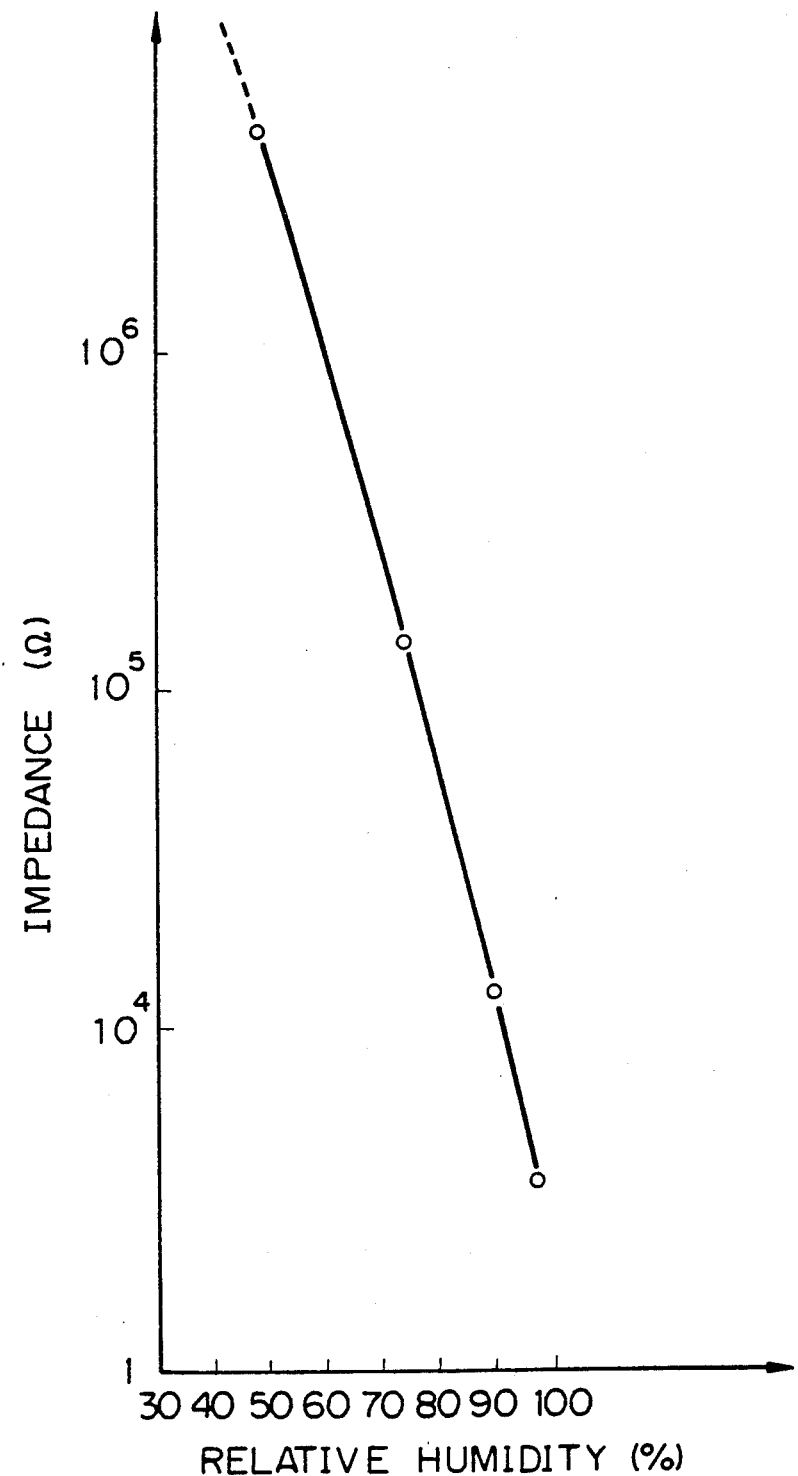
FIG. 25 is the humidity sensing characteristic figure obtained by measuring the samples in Example 17.

Values in Table 5 were plotted on a semilogarithmic graph; FIG. 25. This graph indicates that impedance varies linearly as humidity varies. From this, it may be said that the structure of FIG. 24E is a humidity sensor type.

This method can provide a humidity sensor of very simple and easy-to-build structure. Such products are suitable for "throw-away" articles, such as diapers.

Figure 24F:
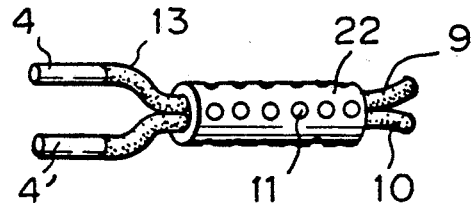
FIG. 24F is a schematic view indicating an example where a heat-shrinkable tube with windows opened is overlaid.

As to the heat-shrinkable tube to cement the contact of the wires with each other, the tube 22 having openings as illustrated in FIG. 24F is also applied. Instead of using a single wire bent into two and bonded, it is, needless to say, also possible to use two wires treated with sensing element and sensing film, and placed in contact with each other.

The humidity sensing element 1 in each of the above mentioned examples, which consists of phosphate coating, covers the whole surface of the metal electrode 9 by means of non-electrolytic or electrolytic conversion treatment.

This method, consisting of simply dipping the metal electrode substrate into a phosphate bath, can yield a coating of uniform thickness.

The phosphate coated on a metal electrode by conversion treatment presents a strong adhesion, and in this coating there are distributed innumerous, extremely fine pores. Such a state is illustrated in FIG. 26.

Figure 26A:
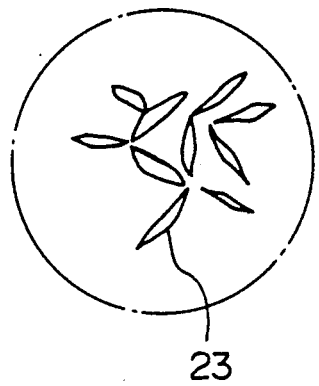
FIG. 26 indicates the status of soluble phosphate made retained within the fine holes, in which 26A is a part of 26B in magnification, 26B is the front view, and 26C is a magnified the vertical section of 26A.
Figure 26B:
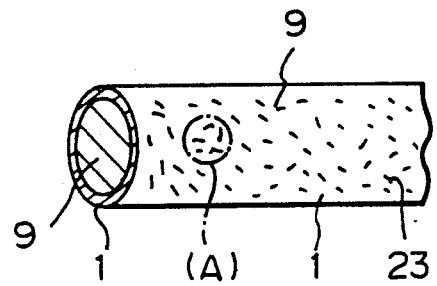
Figure 26C:
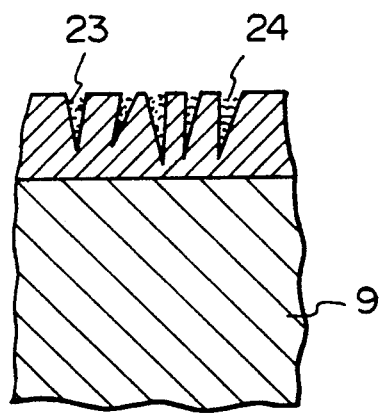

The phosphate coating 1 in FIG. 26B, which is coated on the metal electrode 9, is illustrated in FIG. 26A under magnification. FIG. 26C indicates a section showing fine pores 23 that face in random directions. These pores play the role of footholds by which the humidity sensing film layer to be covered on the coating, is given adhesion through an anchoring effect. Besides this, they are of high hygroscopicity/hydrophilicity, which gives superior humidity sensibility.

As for a phosphate coating which can be made by means of conversion treatment, any one made from one or more of the following can be covered in the metal electrode 9 as a humidity sensing element.

$Zn_3(PO_4)_2.4H_2O$ (Hopeite), $Zn_2Fe(PO_4)_2.4H_2O$ (Phosphophyllite), $Zn_2Ca(PO_4)_2.2H_2O$ (Scholzite), $Zn_3(PO_4)_2.2H_2O$, $AlPO_4\ 2H_2O$, $AlPO_4$; $Fe_3(PO_4)_2.8H_2O$ (Vivianite), $(Mn,Fe)_5H_2OPO_4)_4.4H_2O$ (Hureaulite), $FePO_4.2H_2O$ (Strengite), $Fe_5H_2(PO_4)_4.4H_2O$ (Fe-Hureaulite), $Mn_5H_2(PO_4).4H_2O$ (Mn-Hureaulite), $CaHPO_4.2H_2O$ (Brushite), $CaHPO_4$ (Monetite)

As regards the thickness of the phosphate coating, 0.5 to 12 μ is preferable. In the case of a coating thickness under 0.5 μ thickness where possible loss of continuity may give rise to an exposed portion on the electrode, the humidity sensing film to be formed on this portion comes in contact with the surface with no anchoring effect, resulting in insufficient adhesion. Consequently, when exposed to a repeated wet/dry cycle, the film is split off causing impedance variation.

On the contrary, in the case of film thickness of more than 100 μ, the humidity sensing film formed on it takes a long time to let moisture penetrate thereinto. As a result, impedance is hard to get stabilized and has an excessively large figure: this means inferior function as a humidity sensor.

For the formation of the humidity sensing film layer 13/13' over the humidity sensing element 1 in the case of each Example, a paste was prepared by kneading a mixture comprised of one or more kinds of the above mentioned phosphate powder coatable by conversion treatment, and resin, or resin and water: and was coated and dried/solidified by applying the method as shown in FIG.17; or dipping in a colloidal silica acrylic composite particles emulsion, followed by drying. This method, comprising simply passing a metal electrode through a paste holder makes it possible to get a uniform thickness of the humidity sensing film layer.

Since this layer contains phosphate as the principal component, and the resin formulated therein is moisture-permeable and hydrophilic, it has good humidity sensibility. The underlying phosphate coating, having innumerous fine pores with wide distribution, provides an anchoring effect to which enhances the strength of the adhesion between the underlying coating and the film layer.

Accordingly, as indicated in the example, the film layer functions effectively to concurrently repair defects of current continuity of the underlying coating and elevate the humidity sensitivity. As for the resin used in preparing the paste, organosolvent type resin is also usable. However, watersoluble, thermosetting resin is suitable for the Purpose of this invention, as water is used as a dilutent and the formed film layer is given hydrophilicity.

Phosphate used in preparing the paste is, in most cases, a powder of the same composition as the phosphate coating. If the purpose is to make a variation in the humidity sensing property, such a restriction is not necessary.

Also, as indicated in Example 15, besides those phosphates with a coating composition as provided by conversion treatment, public-known hygroscopic materials such as alkali phosphate, alkali-earth hydrogen phosphate and lithium chloride, glass powder, silica powder, tin oxide powder and chromium oxide powder can be used also by mixing/kneading a mixture of them. This is an easier way to adjust/control the humidity sensing property of the humidity sensor.

It is also possible to use as conversion treatment coating, a chromate conversion coating, such as chromium phosphate coating or a non-chromate coating such as titanium-tannic acid complex salt coating, to build a humidity sensing element.

EXAMPLE 18

FIG. 27 is an example where either one of the electrodes 9, 10 consists of plural twisted wires. As the opposite electrode, in the form of a wire, can be any of the following: iron wire, copper wire, nickel wire, nickel/chromium wire, stainless wire or tungsten wire or any wire which is plated with gold or platinum. This shape allows contact with the humidity sensing element 1 to have smaller resistance, and makes the wire, when twisted, yield elastic pressure on the humidity sensing element, leading to less variation in the contact resistance, and making it suitable for such a function.

The humidity sensing element in Example 15 was used to prepare the electrode having a structure as illustrated in FIG. 27.

Figure 28:
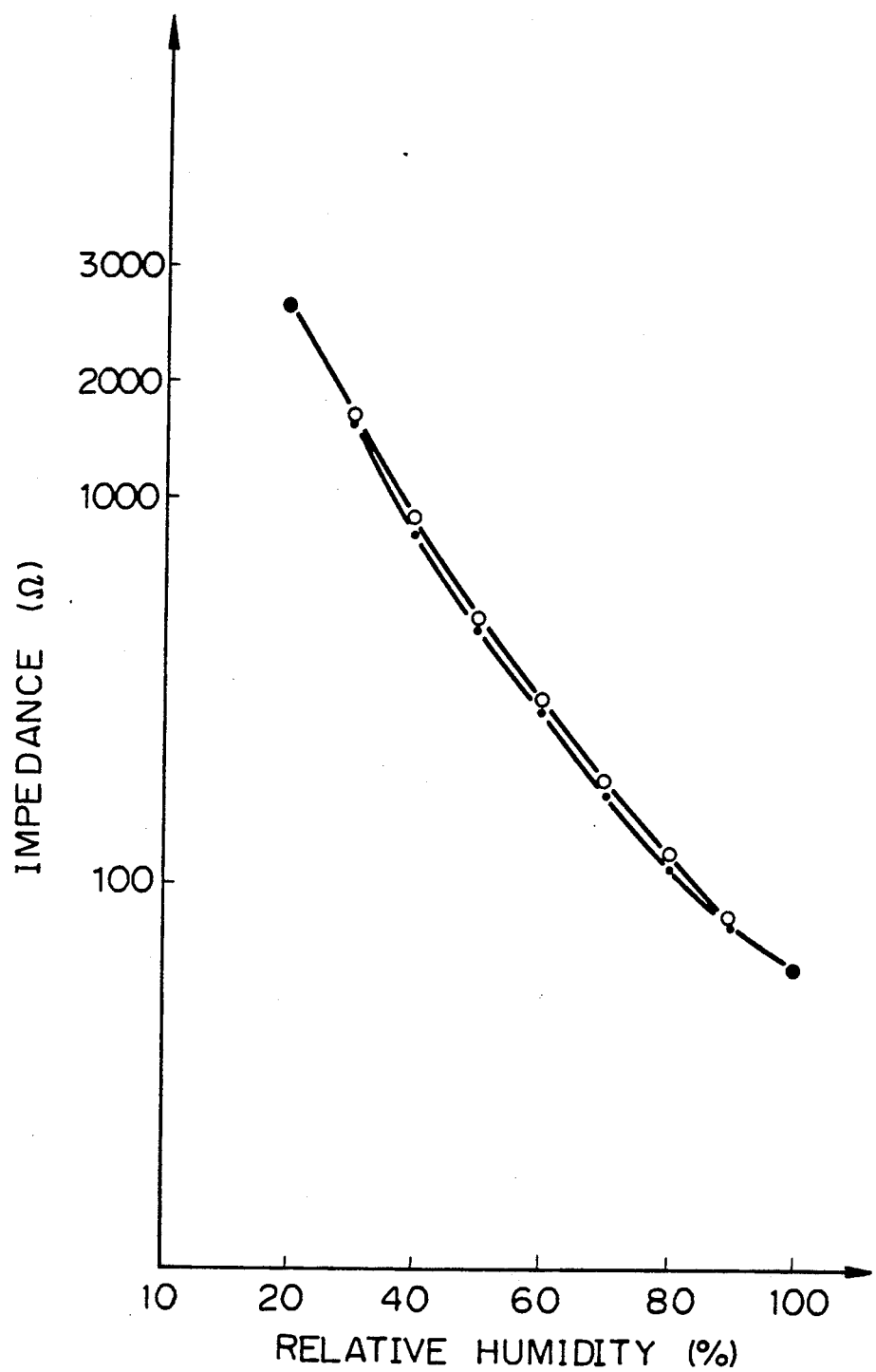
FIG. 28 is the humidity sensing characteristic figure obtained by measuring the samples in Example 18.

This sensor's humidity sensing property is as indicated in FIG. 28. Needless to say, the opposite electrode in this case was metal wire coated with phosphate.

Further, as indicated in FIG. 3, the humidity sensing element consisting of phosphate coating obtained by conversion treatment, largely varies in the impedance on the semilogarithmic graph.

However, it does not dissociates into ions easily at a low is humidity range, and for this reason the magnitude of impedance change in response to humidity change is small. Such inferiority could be successfully overcome by the following method, whereby a modification to a humidity sensing element suitable for a humidity sensor could be made.

That is, with attention paid to the fact that chemical conversion coating has innumerous, extremely fine pores, as noted earlier, potassium metaphosphate, sodium metaphosphate, sodium pyrophosphate, potassium pyrophosphate or a mixture of them, or one or more kinds out of those salts belonging to alkaliearth orthophosphate dihydrate, were made into an aqueous liquid or an alcoholic liquid. In such a liquid, the metal electrode or the opposite electrode coated with phosphate was dipped so as to allow this liquid to penetrate into said fine pores of the coating. After being subjected to water or alcohol vaporization therefrom, watersoluble phosphate was obtained. The watersoluble phosphate retained in those fine pores undergoes dissociation into ions even at low humidity, and functions by decreasing interelectrode impedance, raising the magnitude of impedance change in response to humidity change, and thus becoming capable of sufficiently meeting the requirements to function as a humidity sensing element for a humidity sensor. As to the question of its durability, there is no problem, because the pores are extremely small and phosphate retained therein, even in the form of an aqueous solution, does not flow out.

FIG. 26(A,B,C) shows the fine pores where said watersoluble phosphate is retained.

In the phosphate 7 coated on the metal electrode wire 1 shown in FIG. 26B and FIG. 26A under magnification, there are formed innumerous fine pores 23 facing in random directions, in each of which watersoluble phosphate 24 is retained, as shown in FIG. 26C, a magnified view of a longitudinal section it is also possible to fill in the pores 23 where said phosphate exists, with red oxide ($Fe_2O_3$), magnetic iron oxide ($Fe_3O_4$) in colloidal form or semiconductor oxide. The coating suspension of red oxide in the alcoholic sodium metaphosphate solution on the phosphate-coated surface makes the red oxide powder carried by the alcohol enter the fine pores. When the alcohol evaporates, red oxide powder remains retained together with sodium metaphosphate.

In this way, oxide retained in fine pores is also effective in lowering impedance of a dew sensor as well as in adjusting the sensitivity.

We claim:

1. A humidity sensor comprising at least one metal electrode in effective contact with, as its sensitive element, a chemical conversion coating film selected from the group consisting of:

a phosphate coating comprising at least one of $Zn_3(PO_4)_2.4 H_2O$ (Hopeite), $Zn_2Fe(PO_4)_2.4H_2O$ (Phosphophyllite), $Zn_2Ca (PO_4)_2.2H_2O$ (Scholzite), $Zn_3(PO_4)_2.2H_2O$, $AlPO_4$, $AlPO_4.H_2O$, $Fe_3(PO_4)_2.8H_2O$ (Vivianite), $(Mn,Fe)_5H_2(PO_4)_3.4H_2O$ (Hureanlite), $Mn_5H_2(PO_4)_3.4H_2O$ (Mn-Hureanlite), $Fe_5H_2(PO_4).4H_2O$ (Fe-Hureanlite), $FePO_4.2H_2O$(Strengite), $CaHPO_4.2H_2O$(Brushite), and $CaPO_4$ (Monetite);

an oxalate coating comprising at least one of hydrated $FeC_2O_4$, hydrated $NiC_2O_4$, anhydrous $FeC_2O_4$, and anhydrous $NiC_2O_4$;

a titanium fluoro complex salt coating comprising at least one of $Na_3TiF_6$, $K_3TiF_6$, $(NH_4)_3TiF_6$, $Na_2TiF_6$, $K_2TiF_6$, and $(NH_4)_3TiF_6$;

a chromium phosphate coating;

a chromate coating; and a non-chromate coating comprising at least one of a titanium-tannic acid complex and a zirconium-phytic acid complex;
wherein said chemical conversion coating film is about 0.5 to 12 microns thick which absorbs water and upon water absorption ionizes to an extent sufficient to change its impedance.

2. A humidity sensor according to claim 1, wherein said chromium phosphate coating is a coating formed on an aluminum electrode by applying thereto an acidic solution having a pH of 1.5–3.0 which contains phosphoric acid and chromic acid as the main constituents and fluorine containing compounds.

3. A humidity sensor according to claim 1 wherein said roll-on chromate coating is a coating formed on an aluminum electrode with a roll-on application of treatment solution, which is prepared by adding at least one of colloidal silica or waterborne resin into an acidic solution having a pH of about 1.5 to 3.0 which contains phosphoric acid and chromic acid as the main constituents and fluorine containing compounds.

4. A humidity sensor according to claim 1 wherein the surface of said chemical conversion coating has been post-treated with, a humidity-sensitive material.

5. A humidity sensor according to claim 4 wherein said humidity-sensitive material contains red iron oxide, $Fe_2O_3$.

6. A humidity sensor according to claim 5 including a second electrode made from metal.

7. A humidity sensor as claimed in claim 1 comprising a first and a second electrode and wherein said humidity sensitive chemical conversion coating comprises a first a first surface region in contact with said second electrode and a second surface region exposed to ambient air, and wherein said second electrode extends substantially over said surface regions but is in substantial contact only with said first region.

8. A humidity sensor according to claim 7 wherein said first electrode is prepared by unifying the metal electrode and its electrode terminal lead and said second electrode is built up by unifying the opposite electrode and its terminal lead.

9. A humidity sensor according to claim 7 wherein at least one of said electrodes comprising iron, copper, aluminum, nickel, stainless steel, titanium or their alloys.

10. A humidity sensor according to claim 7 wherein at least one of said electrodes comprise at least one of iron, copper, aluminum, nickel, stainless steel, titanium or steel which have been plated respectively with zinc or tin.

11. A humidity sensor according to claim 9 wherein the metal electrode and opposite electrode are gold plated or platinum plated.

12. A humidity sensor according to claim 7 wherein, over at least one side of the humidity sensitive element, a chemical conversion coating of a humidity sensitive film is formed.

13. A humidity sensor according to claim 12 wherein said chemical conversion coating is a chromate coating or a non-chromate coating.

14. A humidity sensor according to claim 13 wherein said conversion coating is a phosphate coating, selected from the group consisting of $Zn_3(PO_4)_2.4H_2O$ (Hopeite), $Zn_2Fe(PO_4)_2.4H_2O$ (Phosphophillite), $Zn_2Ca(PO_4)_2.2H_2O$ (Scholzite), $Zn_3(PO_4)_2.2H_2O$, $AlPO_4$, $AlPO_4.2H_2O$, $Fe_3(PO_4)_2.8H_2O$ (Vivianite), $(Mn,Fe)_5H_2(PO_4)_3.4H_2O$ (Hureanlite), $Mn_5H_2(PO_4)_3.4H_2O$ (Mn-Hureanlite), $Fe_5H_2(PO_4)_3.4H_2O$ (Fe-Hureaulite), $FePO_4.2H_2O$ (Strengite), $CaHPO_4.2H_2O$ (Brushite) and $CaHPO_4$(Monetite, or a chromate coating of chromium phosphate, or a non-chromate coating of titanium-tannic acid complex or zirconium phytic acid complex.

15. A humidity sensor according to claim 14 wherein said humidity sensible film is a film containing phosphate and resin as the main constituents.

16. A humidity sensor according to claim 15 wherein said phosphate is $Zn_3(PO_4)_2.4H_2O$ (Hopeite), $Zn_2Fe(PO_4)_2.4H_2O$ (Phosphophillite), $Zn_2Ca(PO_4)_2.2H_2O$ (Scholzite), $Zn_3(PO_4)_2.2H_2O$, $AlPO_4$, $AlPO_4.2H_2O$, $Fe_3(PO_4)_2.8H_2O$ (Vivianite), $(Mn,Fe)_5H_2(PO_4)_3.4H_2O$ (Hureanlite), $Mn_5H_2(PO_4)_3.4H_2O$ (Mn-Hureanlite), $Fe_5H_2(PO_4)_3.2H_2O$ (Fe-Hureaulite), $FePO_4.2H_2O$ (Strengite), $CaHPO_4.2H_2O$ (Brushite) and $CaHPO_4$(Monetite), and said resin is thermo-reation type water-soluble urethane resin.

17. A humidity sensor according to claim 15, wherein the conversion coating on the humidity sensitive film an hygroscopic material.

18. A humidity sensor according to claim 17 wherein said humidity sensitive film is a coating formed with the application of colloidal silicon acrylic resin composite particle emulsion.

19. A humidity sensor according to claim 16, claim 17 or claim 18 wherein said humidity sensitive film comprises a moisture permeable paint.

20. A humidity sensor as claimed in claim 4 wherein said humidity sensitive material comprises sodium metaphosphate.

21. A humidity sensor as claimed in claim 5 wherein said humidity sensitive material comprises a semi-conductor oxide.

22. A humidity sensor as claimed in claim 17 wherein said hygroscopic material is at least one of alkali phosphate, alkaline earth dehydrogen orthophosphate, and lithium chloride.

23. A humidity sensor as claimed in claim 1 wherein said film is in the form of a paste.

24. A humidity sensor as claimed in claim 3 wherein said waterborne resin comprises an acrylic resin.

25. A humidity sensor as claimed in claim 7 wherein said coating comprises at least one: of a phosphate coating, an oxalate coating, a titanium fluoro complex coating, a chromium phosphate coating, a roll-on chromate coating, or a non-chromate coating, therebetween and in effective contact with both electrodes.

26. A humidity sensor as claimed in claim 7 having a humidity sensitive chemical conversion coating on both electrodes, each of which coatings having first regions in contact with each other and second regions substantially exposed to ambient air.

27. A humidity sensor as claimed in claim 7 wherein said electrodes are in the form of wires twisted about each other.

28. A humidity sensor as claimed in claim 7 wherein said first electrode has a substantially cylindrical outer surface, and said second electrode is in substantial linear contact with said outer surface.

* * * * *